US009675596B2

(12) United States Patent
Westman et al.

(10) Patent No.: US 9,675,596 B2
(45) Date of Patent: Jun. 13, 2017

(54) 1,2,4-THIAZOLIDIN-3-ONE DERIVATIVES AND THEIR USE IN THE TREATMENT OF CANCER

(71) Applicant: Baltic Bio AB, Umea (SE)

(72) Inventors: Jacob Westman, Jarlasa (SE); Allan Hallett, Welwyn Garden City (GB); Jan Vagberg, Sollentuna (SE)

(73) Assignee: Baltic Bio AB, Umea (SE)

( * ) Notice: Subject to any disclaimer, the term of this patent is extended or adjusted under 35 U.S.C. 154(b) by 0 days.

(21) Appl. No.: 14/883,190

(22) Filed: Oct. 14, 2015

(65) Prior Publication Data

US 2016/0128993 A1  May 12, 2016

Related U.S. Application Data

(62) Division of application No. 13/381,426, filed as application No. PCT/GB2010/001315 on Jul. 8, 2010, now Pat. No. 9,162,994.

(60) Provisional application No. 61/213,735, filed on Jul. 8, 2009.

(51) Int. Cl.
| C07D 285/08 | (2006.01) |
| C07D 417/10 | (2006.01) |
| C07D 417/12 | (2006.01) |
| A61K 31/433 | (2006.01) |
| A61K 31/4439 | (2006.01) |
| A61P 3/10 | (2006.01) |

(52) U.S. Cl.
CPC ........ *A61K 31/4439* (2013.01); *A61K 31/433* (2013.01); *C07D 285/08* (2013.01); *C07D 417/10* (2013.01); *C07D 417/12* (2013.01)

(58) Field of Classification Search
CPC .. C07D 285/08; C07D 417/10; C07D 417/12; A61K 31/433; A61K 31/4439
See application file for complete search history.

(56) References Cited

U.S. PATENT DOCUMENTS

| 4,093,624 A | 6/1978 | Revankar et al. |
| 2003/0195238 A1 | 10/2003 | Gil et al. |

FOREIGN PATENT DOCUMENTS

| WO | WO-01/85685 A1 | 11/2001 |
| WO | WO-2006/045581 A1 | 5/2006 |
| WO | WO-2007/010273 A2 | 1/2007 |
| WO | WO-2007/010281 A2 | 1/2007 |
| WO | WO-2008/090356 A1 | 7/2008 |

OTHER PUBLICATIONS

Buchwald et al., *J. Am. Chem. Soc.* (1994), 116, 7901-7902.
Buchwald et al., *Org. Process Res. Dev.* (2006) 10(4), 762-769.
Calle and Kaaks (2004), *Nature Reviews Cancer*, 4, 579-591.
Castaño T., et al., *Bioorganic & Medicinal Chemistry* 16 (2008) 6193-6206.
Castro et al., *Bioorg. Med. Chem.* 2008, 16, 495-510.
Cho et al., *J. Heterocyclic Chem.* 1991, 28, 1645-1649.
Document cited as XP-002611425 in international search report (Extract from Shaban, M. E. et al., *Egyptian Journal of Chemistry*, vol. 43, No. 2, 2000, 147-163).
Document cited as XP-002611426 in international search report (Extract from Bhagat, S. K. et al., *Indian Journal of Heterocyclic Chemistry*, vol. 9, No. 3, 2000, 237-238).
Document cited as XP-002611427 in international search report (Extract from Shi, Da-Qing et al., *Youji Huazxue*, vol. 15, No. 6, 1995, 615-618).
Document cited as XP-002611429 in international search report (Extract from Pandey, A. K. et al., *Indian Journal of Chemistry, Section B: Organic Chemistry including medicinal chemistry*, vol. 21B, No. 2, 1982, 150-152).
Document cited as XP-002611430 in international search report.
Encinas A., et al., *Eur. J. Org. Chem.* 2007, 5603-5608.
Foroumadi et al., *Arch. Pharm. Chem. Life Sci.* (2005) 338, 112-116.
Foroumadi et al., *Arzneim. Forsch.* (1999) 49, 1035-1038.
Fouli, F. A. et al., *Journal Fuer Praktische Chemie*, vol. 329, No. 2, 1987, 203-208.
Hammarsten and Högstedt (2005) *European Journal of Cancer*, 41, 2887.
Han S., et al., *Mol. Cancer Ther.*, 5, 430 (2006).
Hardie, *Genes & Development*, 25: pp. 1895-1908 (2011).
Hardy et al., *J. Biol. Chem.* (2005) 280, 13285.
Hartwig et al., *J. Am. Chem. Soc.* (1994), 116, 5969-5970.
http://www.ncbi.nlm.nih.gov/projects/geo/gds/gds_browse.cgi?gds=1263.
Hurst, D. T. et al., *Aust. J. Chem.* 1998, 41, 1221.
Jones et al., *Molecular Cell*, vol. 18, pp. 283-293 (2005).
Katritsky et al., *ARKIVOC (Archive for Organic Chemistry)* 2003 (viii) 8-14.
Kaugars et al., *J. Org. Chem.* 1979, 44(22), 3840-3843.
Keilen et al., *Acta Chem. Scand.* 1988, B42, 362-366.
L'Abbe G., et al., *Journal of Heterocyclic Chemistry*, 1990, 27(4), 1059-1062.
L'Abbe G., et al., *Journal of Heterocyclic Chemistry*, 1990, 27, 2133-2138.
Liang et al., *Nature Cell Biology*, vol. 9, No. 2. pp. 218-224 and supplementary information (2007).
Ma et al, *Cancer Cell* (2004) 6, 445.
Manna P., et al., *Int. J. Cancer*, 2005, 113(4), 549-560.
Martinez et al., *Bioorg. Med. Chem.* 1997, 7, 1275-1283.
Warburg O., *Science* (1956) 123, 3191, 309-314.
Xu et al., *Tetrahedron Lett.* 1998, 39, 1107-1110.

(Continued)

*Primary Examiner* — Sahar Javanmard
(74) *Attorney, Agent, or Firm* — McCarter & English, LLP; Steven G. Davis; Mei Bai

(57) ABSTRACT

According to the invention there is provided a compound of formula (I) wherein: A represents C(=N—W-D) or S; B represents S or C(—NH—W-D); when: A represents C(=N—W-D) and B represents S then the bond between B and the NH atom is a single bond; or A represents S and B represents C(—NH—W-D) then the bond between B and the NH atom is a double bond; X represents -Q-[CR$^x$R$^y$]$_n$—; W represents —[CR$^x$R$^y$]$_m$— or —C(O)—[CR$^x$R$^y$]$_p$—; Q represents a bond, —N(R$^a$)—; —S—, or —O—; A$_1$ to A$_5$ respectively represent C(R$^1$), C(R$^2$), C(R$^3$), C(R$_4$) and C(R$^5$), or, alternatively, up to two of A$_1$ to A$_5$ may independently represent N; D represents phenyl, pyridyl or pyrimidinyl optionally substituted by one or more R$^6$ groups, which compounds are useful in the treatment of cancer.

14 Claims, 3 Drawing Sheets

(56) References Cited

OTHER PUBLICATIONS

Figure 1:
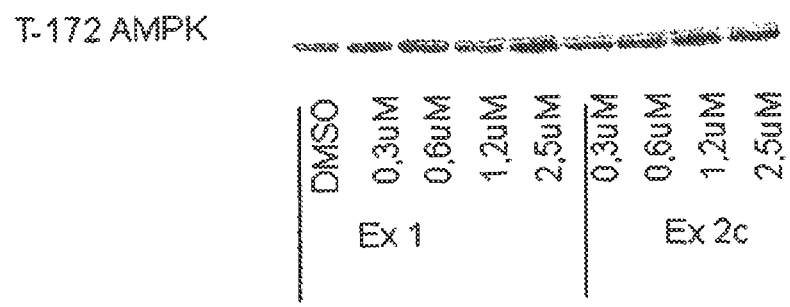

Yao C.-J., et al., *Int. J. Cancer*, 118, 773 (2006).
Zakikhani M., et al., *Cancer Res.*, 66, 10269 (2006).
Viollet et al., *Front. Biosci.*, 2009, 14:3380-3400.
Yu L.-F. et al., *Current Topics in Medicinal Chemistry*, 2010, 10, 397-410.
Bruckbauer, et al., Synergistic effects of metformin, resveratrol, and hydroxymethylbutyrate on insulin sensitivity, Diabetes Metab Syndr Obes. 2013;6:93-102.
Cool, et al., Identification and characterization of a small molecule AMPK activator that treats key components of type 2 diabetes and the metabolic syndrome, Cell Metab. 2006;3(6):403-16.
Groenendijk, et al., Sorafenib synergizes with metformin in NSCLC through AMPK pathway activation, Int J Cancer. 2015;136(6):1434-44.
Rattan, et al., 5-Aminoimidazole-4-carboxamide-1-beta-D-ribofuranoside inhibits cancer cell proliferation in vitro and in vivo via AMP-activated protein kinase, J Biol Chem. 2005;280(47):39582-93.
Zhang, L., et al., *J. Biol. Chem.* 2011, 286 (19):16879-16890.
Guzman, M.L., et al., *Blood*, vol. 110, No. 13, 2007, 4436-4444.
Cai, Z., et al., *J. Alzheimer's*, 2012, 89-98.
King, T.D., et al., *Biochem. Pharmacol.* 2006, 71 (11):1637-1647.
Javadov, S., et al., *J. Molecular and Cellular Cardiology* 46, 2009, 998-1007.
Greco, S.J., et al., *Neuroscience Letters* 455, 2009, 191-194.

PC-3 cells 24h starvation, 4h treatment

Dephosphorylation assay Ex 1 vs. Ex 2c

1,2,4-THIAZOLIDIN-3-ONE DERIVATIVES AND THEIR USE IN THE TREATMENT OF CANCER

This application is a divisional application of U.S. application Ser. No. 13/381,426, filed Apr. 4, 2012, which is a U.S. National Stage of International Application Serial No. PCT/GB2010/001315, filed Jul. 8, 2010, which claims the benefit of U.S. Provisional Application Ser. No. 61/213,735, filed Jul. 8, 2009.

FIELD OF THE INVENTION

This invention relates to pharmaceutically-useful compounds. The invention also relates to the use of such compounds in the treatment of cancer.

BACKGROUND

AMP-activated protein kinase (AMPK) represents a new target for the treatment of several diseases, including cancer.

Excess adiposity is associated to different degrees with an increased risk of developing cancers, such as colorectal adenomas, breast cancer (postmenopausal), endometrial cancer, kidney cancer, oesophageal adenocarcinoma, ovarian cancer, prostate cancer, pancreatic cancer, gallbladder cancer, liver cancer and cervical cancer (Calle and Kaaks (2004), *Nature Reviews Cancer*, 4, 579-591).

Investigations have demonstrated that cancer cells require high rates of fatty acid and protein synthesis for their invasive growth and survival. Studies have shown that inhibition of cancer cell proliferation is possible using AMPK activators. The effects are associated with down-regulation of mTOR and eEF2. AMPK activators also suppress lipid synthesis in tumour cells. It has also been shown that it is a link between AMPK and other anti-cancer targets such as LKB1 and caspase-3 activation.

Cancer cells use glucose at a higher rate compared to normal cells (Warburg O, 1956). Instead of mitochondrial oxidative phosphorylation to produce ATP, cancer cells metabolise glucose via hydrolysis.

Recent studies suggest that hyperinsulinemia is correlated among other things to the incidence of colon and lethal breast and prostate cancer.

Elevated plasma free fatty acids (FFAs) stimulate pancreatic β-cells and is one cause of hyperinsulinemia.

In prostate cancer, hyperinsulinemia has been shown to be prospective risk factor for death and data support that the insulin level could be used as a marker of prostate cancer prognosis (Hammarsten and Högstedt (2005) *European Journal of Cancer*, 41, 2887).

Several mechanisms may link hyperinsulinemia to the incidence and outcome of breast cancer. Firstly, chronic hyperinsulinemia results in increased production of ovarian testosterone and oestrogen and inhibition of hepatic production of sex hormone binding globulin, a sex-hormonal profile that is associated with breast cancer. Secondly, hyperinsulinemia suppresses hepatic production of insulin-like growth factor binding protein-1 (IGFBP-1), and thus increases circulating levels of IGF-1, which has potent mitogenic effect on breast tissue. Thirdly, insulin itself may have a direct mitogenic effect on breast cancer cells.

The study by Hardy et al ((2005), *J. Biol. Chem.* 280, 13285) shows that FFAs directly stimulate the growth of breast cancer cells in a GPR40 dependent manner. Moreover, expression studies performed on tumor tissue isolated from 120 breast cancer patient shows a frequent expression of GPR40 emphasizing the clinical relevance of the findings of Hardy (see, for example, Ma et al, *Cancer Cell* (2004) 6, 445).

Another expression study on clinical material from colon cancer patients suggests that similar mechanisms could be relevant also in these malignancies (see http://www.ncbi.nlm.nih.gov/projects/geo/gds/gds_browse.cgi?gds=263).

Cancer cells in general exhibit an aberrant metabolism compared to non-transformed cells. Neoplastic cells synthesise lipids to a much larger extent than their normal counterparts and metabolise glucose differently. It has been suggested that this aberrant metabolism constitutes a therapeutic target. By interfering with one or, preferably, several of the pathways controlling cellular metabolism, cancer cells would be more sensitive than non-transformed cells, thus creating a therapeutic window. Examples of pathways/targets include glycolysis interfering agents, lipid synthesis pathway, AMPK activating agents and agents affecting mitochondrial function.

AMP-activated protein kinase (AMPK) is a protein kinase enzyme that consists of three protein sub-units and is activated by hormones, cytokines, exercise, and stresses that diminish cellular energy state (e.g. glucose deprivation). Activation of AMPK increases processes that generate adenosine 5'-triphosphate (ATP) (e.g., fatty-acid oxidation) and restrains others such as fatty acid-, glycerolipid- and protein-synthesis that consume ATP, but are not acutely necessary for survival. Conversely, when cells are presented with a sustained excess of glucose, AMPK activity diminishes and fatty acid-, glycerolipid- and protein-synthesis are enhanced. AMPK thus is a protein kinase enzyme that plays an important role in cellular energy homeostasis. Therefore, the activation of AMPK is coupled to glucose lowering effects and triggers several other biological effects, including the inhibition of cholesterol synthesis, lipogenesis, triglyceride synthesis, and the reduction of hyperinsulinemia.

Given the above, AMPK is a preferred target for the treatment of the metabolic syndrome and especially type 2 diabetes. AMPK is also involved in a number of pathways that are important for many different diseases (e.g. AMPK is also involved in a number of pathways that are important in CNS disorders, fibrosis, osteoporosis, heart failure and sexual dysfunction).

AMPK is also involved in a number of pathways that are important in cancer. Several tumour suppressors are part of the AMP pathway. AMPK acts as a negative regulator of the mammalian TOR (mTOR) and EF2 pathway, which are key regulators of cell growth and proliferation. The deregulation may therefore be linked to diseases such as cancer (as well as diabetes). AMPK activators may therefore be of utility as anti-cancer drugs.

Current anti-diabetic drugs (e.g. metformin, glitazones) are known to not be significantly potent AMPK activators, but only activate AMPK indirectly and with low efficacy. However, due to the biological effects of AMPK activation at the cell level, compounds that are AMPK activators, and preferably direct activators of AMPK, may find utility as anti-cancer drugs, as well as for the treatment of many other diseases.

The listing or discussion of an apparently prior-published document in this specification should not necessarily be taken as an acknowledgement that the document is part of the state of the art or is common general knowledge.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Keilen et al., *Acta Chem. Scand.* 1988, B42, 362-366 describe the formation of 1,2,4-thiadiazolo activated pyrimidinones. There is also disclosed a specific 1,2,4-thiadiazolo-3-ones. However, the document does not disclose any biological effects associated with the disclosed compounds, nor does it disclose 1,2,4-thiadiazolo-3-ones substituted at the 5-position with an amide or amine derivative bearing at least one substituted aromatic ring.

Kaugars et al., *J. Org. Chem.* 1979, 44(22), 3840-3843 describe 5-phenyl- and 5-methyl-substituted phenyl urea derivatives of 1,2,4, thiadiazol-3-one that are substituted in the 2-position with a methyl group. There is no mention of any biological effects associated with the disclosed compounds.

Cho et al *J. Heterocyclic Chem.* 1991, 28, 1645-1649 discloses various 1,2,4-thiadiazol-3-ones. However, there is no disclosure of such 1,2,4-thiadiazol-3-ones, in which the 2-position and 5-position contain substituents bearing an aromatic ring.

U.S. Pat. No. 4,093,624 describes 1,2,4 thiadiazolidin-3-one compounds, described as having antimicrobial activity, which are substituted by a —$NH_2$ or —NHAc in the 5-position and H or ribofuranosyls in the 2-position. There is no disclosure of 1,2,4-thiadiazol-3-ones in which the 2-position and 5-position contain substituents bearing an aromatic ring.

Castro et al., *Bioorg. Med. Chem.* 2008, 16, 495-510 describes thiadiazolidinone derivates as GSK-3β ☐inhibitors that are potentially useful for the treatment of Alzheimer's disease. There is no mention that such compounds may be useful as AMPK activators. Further, there is no mention of 1,2,4-thiadiazol-3-ones substituted at the 5-position with an amide or amine derivative bearing at least one substituted aromatic ring.

Martinez et al. *Bioorg. Med. Chem.* 1997, 7, 1275-1283 describes arylimino-1,2,4-thiadiazolidinone derivatives as potassium channel openers that are potentially useful for the treatment of diseases involving smooth muscle contraction (e.g. hypertension). However, there is no disclosure of such thiadiazolidinones substituted at the 2-position with an aromatic group.

US patent application publication number 2003/0195238 describes thiadiazolidine derivates as GSK-3β ☐inhibitors that are potentially useful for the treatment of Alzheimer's disease. However, this document mainly relates to thiadiazolidines substituted by two carbonyl/thiocarbonyl groups (thereby forming e.g. a 3,5-dioxo-thiadiazolidine or a 3-thioxo-5-oxo-thiadiazolidine). Further, it mainly relates to compounds in which both nitrogen atoms of the thiadiazolidine are substituted. The document does not relate to thiadiazolidines substituted at the 2-position with a group bearing an aromatic group and at the 5-position with an amino or amido derivative bearing an aromatic group.

International patent applications WO 2007/010273 and WO 2007/010281 both disclose e.g. thiazolidin-4-one and 1,1-dioxo-1,5-dihydro-[1,4,2]dithiazole compounds that are able to antagonize the stimulatory effect of FFAs on cell proliferation when tested in an assay using a human breast cancer cell line (MDA-MB-231). Such compounds are thus indicated in the treatment of cancer and/or as modulators of FFAs. However, these documents do not disclose or suggest thiadiazolidinones.

DISCLOSURE OF THE INVENTION

According to embodiments of the invention, there is provided a compound of formula I,

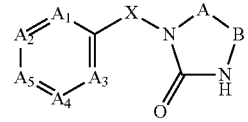

wherein:
A represents C(=N—W-D) or S;
B represents S or C(—NH—W-D);
when:
A represents C(=N—W-D) and B represents S then the bond between B and the NH atom is a single bond; or
A represents S and B represents C(—NH—W-D) then the bond between B and the NH atom is a double bond;
X represents -Q-[$CR^xR^y$]$_n$—;
W represents —[$CR^xR^y$]$_m$— or —C(O)—[$CR^xR^y$]$_p$—;
Q represents a bond, —N($R^a$)—, —S—, or —O—;
$A_1$ to $A_5$ respectively represent C($R^1$), C($R^2$), C($R^3$), C($R^4$) and C($R^5$), or, alternatively, up to two of $A_1$ to $A_5$ may independently represent N;
D represents phenyl, pyridyl or pyrimidinyl optionally substituted by one or more $R^6$ groups;
$R^x$ and $R^y$, on each occasion when used herein, are independently selected from H, halo, $C_{1-6}$ alkyl (optionally substituted by one or more halo atoms), aryl (optionally substituted by one or more halo atoms) or $R^x$ and $R^y$ are linked to form, along with the carbon atom to which they are attached, a non-aromatic 3- to 8-membered ring, optionally containing 1 to 3 heteroatoms selected from O, S and N, which ring is itself optionally substituted by one or more substituents selected from halo or $C_{1-6}$ alkyl (optionally substituted by one or more halo atoms);
$R^1$ to $R^5$ independently represent H, halo, —$R^7$, —$CF_3$, —CN, —$NO_2$, —C(O)$R^7$, —C(O)O$R^7$, —C(O)—N($R^{7a}$)$R^{7b}$, —N($R^{7a}$)$R^{7b}$, —N($R^7$)$_3^+$, —S$R^7$, —O$R^7$, —NH(O)$R^7$, —$SO_3R^7$, aryl or heteroaryl (which aryl and heteroaryl groups are themselves optionally and independently substituted by one or more groups selected from halo and $R^{16}$), or any two of $R^1$ to $R^5$ which are adjacent to each other are optionally linked to form, along with two atoms of the essential benzene ring in the compound of formula I, an aromatic or non-aromatic 3- to 8-membered ring, optionally containing 1 to 3 heteroatoms selected from O, S and N, which ring is itself optionally substituted by one or more substituents selected from halo, —$R^7$, —O$R^7$ and =O;
$R^6$ independently represents, on each occasion when used herein, cyano, —$NO_2$, halo, —$R^8$, —O$R^8$, —N($R^8$)C(O)$R^8$, —N$R^9R^{10}$, —S$R^{11}$, —Si($R^{12}$)$_3$, —OC(O)$R^{13}$, —C(O)O$R^{13}$, —C(O)$R^{14}$, —C(O)N$R^{15a}R^{15b}$, —S(O)$_2$N$R^{15c}R^{15d}$, aryl or heteroaryl (which aryl and heteroaryl groups are themselves optionally and independently substituted by one or more groups selected from halo and $R^{16}$), or any two $R^6$ groups which are adjacent to each other are optionally linked to form, along with two atoms of the essential benzene ring in the compound of formula I, an aromatic or non-aromatic 3- to 8-membered ring, optionally containing 1 to 3 heteroatoms selected from O, S and N, which ring is itself optionally substituted by one or more substituents selected from halo, —$R^7$, —O$R^7$ and =O;
$R^7$, on each occasion when used herein, is selected from H or $C_1$-$C_6$ alkyl, $C_1$-$C_6$ cycloalkyl, aryl and heteroaryl (wherein the latter four groups are optionally substituted by one or more halo atoms);
$R^{7a}$ and $R^{7b}$ are independently selected from H, or $C_1$-$C_6$ alkyl, $C_1$-$C_6$ cycloalkyl, aryl and heteroaryl, or $R^{7a}$ and $R^{7b}$ are optionally linked to form, along with the nitrogen atom to which they are attached, an aromatic or non-aromatic 3- to 8-membered ring, optionally containing 1 to 3 heteroatoms selected from O, S and N, which ring is itself optionally substituted by one or more substituents selected from halo, —$R^7$, —$OR^7$ and =O;

$R^a$, $R^8$, $R^9$, $R^{10}$, $R^{11}$, $R^{12}$, $R^{13}$, $R^{14}$, $R^{15a}$, $R^{15b}$, $R^{15c}$ and $R^{15d}$, on each occasion where used herein, independently represent H or $R^{16}$;

$R^{16}$ represents, on each occasion when used herein, $C_{1-6}$ alkyl optionally substituted by one or more halo atoms;

n represents 0 or, more preferably, 1 or 2;

m represents 2 or, more preferably, 1 or 0;

p represents 2 or, more preferably, 1 or 0;

or a pharmaceutically-acceptable salt or solvate, or a pharmaceutically functional derivative thereof, provided that when D is phenyl, then at least one of $A_1$ to $A_5$ is not (C—H) and/or D is substituted by one or more —$R^6$ groups.

Pharmaceutically-acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

"Pharmaceutically functional derivatives" of compounds of formula I as defined herein includes ester derivatives and/or derivatives that have, or provide for, the same biological function and/or activity as any relevant compound. Thus, for the purposes of this invention, the term also includes prodrugs of compounds of formula I.

The term "prodrug" of a relevant compound of formula I includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxy or carbonyl group in a compound of formula I is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elsevier, New York-Oxford (1985).

Compounds of formula I, as well as pharmaceutically-acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention. For example, the following tautomers are included within the scope of the invention:

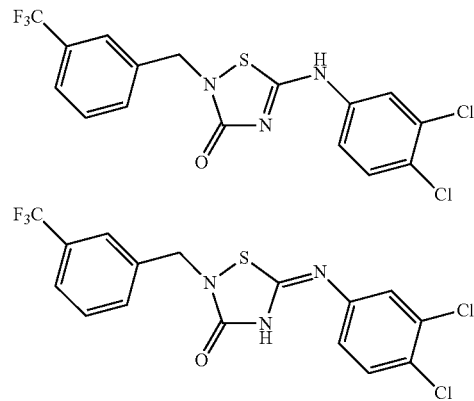

Compounds of formula I contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halo atoms). Where the term "alkyl" refers to an acyclic group, it is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably $C_{3-12}$ cycloalkyl and, more preferably, $C_{5-10}$ (e.g. $C_{5-7}$) cycloalkyl.

When used herein, alkylene refers to $C_{1-10}$ (e.g. $C_{1-6}$) alkylene and, preferably $C_{1-3}$ alkylene, such as pentylene, butylene (branched or unbranched), preferably, propylene (n-propylene or isopropylene), ethylene or, more preferably, methylene (i.e. —$CH_2$—).

The term "halogen", when used herein, includes fluorine, chlorine, bromine and iodine.

The term "aryl" when used herein includes $C_{6-14}$ (such as $C_{6-13}$ (e.g. $C_{6-10}$)) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Most preferred aryl groups include phenyl.

The term "heteroaryl" when used herein refers to an aromatic group containing one or more heteroatom(s) (e.g. one to four heteroatoms) preferably selected from N, O and S (so forming, for example, a mono-, bi-, or tricyclic heteroaromatic group). Heteroaryl groups include those which have between 5 and 14 (e.g. 10) members and may be monocyclic, bicyclic or tricyclic, provided that at least one of the rings is aromatic. However, when heteroaryl groups are bicyclic or tricyclic, they are linked to the rest of the molecule via an aromatic ring. Heterocyclic groups that may be mentioned include benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Particularly preferred heteroaryl groups include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, thiophenyl, pyranyl, carbazolyl, acridinyl, quinolinyl, benzoimidazolyl, benzthiazolyl, purinyl, cinnolinyl and pteridinyl. Particularly preferred heteroaryl groups include monocylic heteroaryl groups.

For the avoidance of doubt, in cases in which the identity of two or more substituents in a compound of formula I may be the same, the actual identities of the respective substituents are not in any way interdependent. For example, given that D may be optionally substituted by one or more $R^6$ groups, then those $R^6$ groups may be the same or different. Similarly, in the situation in which $R^6$ and $R^7$ are both aryl groups substituted by one or more $C_{1-6}$ alkyl groups, the alkyl groups in question may be the same or different. Additionally, in the situation in which $R^8$, $R^9$, $R^{10}$, $R^{11}$, $R^{12}$, $R^{13}$, $R^{14}$, $R^{15a}$, $R^{15b}$, $R^{15c}$ and $R^{15d}$ independently represent $R^{16}$ then those $R^{16}$ groups may be the same or different.

For the avoidance of doubt, when a term such as "$A_1$ to $A_5$" is employed herein, this will be understood by the skilled person to mean any of (i.e. some or all, as applicable) $A_1$, $A_2$, $A_3$, $A_4$ and $A_5$ inclusively.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that in certain preferred embodiments of the compounds of the invention, some or all of the provisos (a) to (c) above will become redundant (for example, where it is stated that at least one (or both) of the $A_1$ to $A_5$-containing ring and/or ring D carries a substituent other than hydrogen, then all of the provisos (a) to (c) above are redundant).

In an embodiment of the invention, there is provided a compound of formula I wherein: A represents C(=N—W-D) and W represents —C(O)—$[CR^xR^y]_p$—.

In a further embodiment of the invention, there is provided a compound of formula I wherein:
A represents C(=N—W-D) and W represents —$[CR^xR^y]_m$—.

In yet a further embodiment of the invention, there is provided a compound of formula I wherein:
B represents C(—NH—W-D) and W represents —C(O)—$[CR^xR^y]_p$—.

In a yet further embodiment of the invention, there is provided a compound of formula I wherein:
B represents C(—NH—W-D) and W represents —$[CR^xR^y]_m$—.

Preferred compounds of formula I include those in which at least one of $A_1$ to $A_5$ is not (C—H) and D is substituted by one or more —$R^6$ groups. It is preferred that either the $A_1$ to $A_5$-containing ring or ring D is substituted with a substituent other than H.

When it is stated herein that at least one of $A_1$ to $A_5$ is not (C—H) or that ring D is substituted with a substituent other than H, we mean that either:
one of $A_1$ to $A_5$ represents N or, preferably, one of $A_1$ to $A_5$ represents $C(R^1)$, $C(R^2)$, $C(R^3)$, $C(R^4)$ or $C(R^5)$ (as appropriate) in which at least one of $R^1$, $R^2$, $R^3$, $R^4$ or $R^5$ represents a substituent other than H (i.e. at least one of $R^1$ to $R^5$ substituent is present that represents halo, —$R^7$, —$CF_3$, —CN, —$NO_2$, —$C(O)R^7$, —$C(O)OR^7$, —$C(O)$—$N(R^{7a})R^{7b}$, —$N(R^{7a})R^{7b}$, —$N(R^7)_3^+$, —$SR^7$, —$OR^7$, —NH(O)$R^7$, —$SO_3R^7$, aryl or heteroaryl (which aryl and heteroaryl groups are themselves optionally and independently substituted by one or more groups selected from halo and $R^{16}$), or any two of $R^1$ to $R^5$ which are adjacent to each other are linked as defined herein); or ring D represents pyridyl or pyrimidinyl or, preferably, ring D is substituted by one or more $R^6$ groups.

More preferred compounds of formula I that may be mentioned include those in which: one of $A_1$ to $A_5$ represents N or, preferably, one of $A_1$ to $A_5$ represents $C(R^1)$, $C(R^2)$, $C(R^3)$, $C(R^4)$ or $C(R^5)$ (as appropriate) in which at least one of $R^1$, $R^2$, $R^3$, $R^4$ or $R^5$ represents a substituent other than H (e.g. a substituent as defined herein); and ring D represents pyridyl or pyrimidyl or, preferably, ring D is phenyl substituted by one or more $R^6$ groups.

Preferred compounds of formula I that may be mentioned include those in which: A represents S.

More preferred compounds of formula I that may be mentioned include those in which: B represents S.

Compounds of formula I that may be mentioned include those in which:

each —[$CR^xR^y$]— unit may be independently selected from:
(a) a unit wherein $R^x$ and $R^y$ are independently selected from H, halo, $C_{1-6}$ alkyl (optionally substituted by one or more halo atoms); and
(b) a unit wherein $R^x$ and $R^y$ are linked to form, along with the carbon atom to which they are attached, a non-aromatic 3- to 8-membered ring, optionally containing 1 to 3 heteroatoms selected from O, S and N, which ring is itself optionally substituted by one or more substituents selected from halo or $C_{1-6}$ alkyl (optionally substituted by one or more halo atoms), provided that no more than one unit is selected from (b); (e.g. each —[$CR^xR^y$]— unit may be independently selected from:
(a) a unit wherein $R^x$ and $R^y$ are independently selected from H, halo, $C_{1-3}$ alkyl (optionally substituted by one or more halo atoms) (e.g. at least one of $R^x$ and $R^y$ is H);
(b) a unit wherein $R^x$ and $R^y$ are linked to form, along with the carbon atom to which they are attached, a non-aromatic ring selected from cyclobutyl, cyclopentyl, cyclohexyl or, more particularly, cyclopropyl, which ring is itself optionally substituted by one or more substituents selected from halo or $C_{1-6}$ alkyl (optionally substituted by one or more halo atoms), provided that no more than one unit is selected from (b)).

Compounds of formula I that may be mentioned include those in which:

$R^x$ and $R^y$ are linked to form, along with the carbon atom to which they are attached, a non-aromatic 3- to 8-membered ring, optionally containing 1 to 3 heteroatoms selected from O, S and N, which ring is itself optionally substituted by one or more substituents selected from halo and/or $C_{1-6}$ alkyl (optionally substituted by one or more halo atoms).

Further compounds of formula I that may be mentioned include those in which:

$R^x$ and $R^y$ are linked to form, along with the carbon atom to which they are attached, a cyclobutyl, cyclopentyl, cyclohexyl or, more preferably, cyclopropyl ring which ring is itself optionally substituted by one or more substituents selected from halo and/or $C_{1-6}$ alkyl (optionally substituted by one or more halo atoms, or more preferably unsubstituted).

Further compounds of formula I that may be mentioned include those in which:

one —[$CR^xR^y$]— unit forms a non-aromatic 3- to 8-membered ring, optionally containing 1 to 3 heteroatoms selected from O, S and N, which ring is itself optionally substituted by one or more substituents selected from halo or $C_{1-6}$ alkyl (optionally substituted by one or more halo atoms) and, if other —[$CR^xR^y$]— units are present, then the additional $R^x$ and $R^y$ groups are independently selected from H, halo, $C_{1-6}$ alkyl (optionally substituted by one or more halo atoms) or aryl (optionally substituted by one or more halo atoms).

Further compounds of formula I that may be mentioned include those in which:

one —[$CR^xR^y$]— unit is linked to form a cyclobutyl, cyclopentyl, cyclohexyl or, more preferably, cyclopropyl ring which ring is itself optionally substituted by one or more substituents selected from halo or $C_{1-6}$ alkyl (optionally substituted by one or more halo atoms, or more preferably unsubstituted) and, if other —[$CR^xR^y$]— units are present, then the additional $R^x$ and $R^y$ groups are independently selected from phenyl (optionally substituted by one or more halo atoms) or, more preferably, H, halo, $C_{1-6}$ alkyl (optionally substituted by one or more halo atoms).

The above preferences for —[$CR^xR^y$]— apply particularly in respect of those compounds in which the relevant unit is part of the substituent X.

Compounds of formula I that may be mentioned include those in which:

$R^x$ and $R^y$ are independently selected from phenyl (optionally substituted by one or more halo atoms) or, more preferably, H, halo, $C_{1-6}$ alkyl (optionally substituted by one or more halo atoms).

Further compounds of formula I that may be mentioned include those in which:

Q represents —S—, preferably, —N($CH_3$)—, —O— or, more preferably, a bond.

Compounds of formula I that may be mentioned include those in which:

when X represents -Q-[$CR^xR^y$]$_n$—, then the —[$CR^xR^y$]$_n$— moiety preferably represents —$CR^xR^y$— (e.g. —$CH_2$—, —C(—$CH_2CH_2$—)—, i.e. —C(cyclopropyl)-, or —C(H)(aryl)-) or —[$CR^xR^y$]$_2$— (e.g. —$CH_2CH_2$—):

when n represents 1, then $R^x$ and $R^y$ independently represent $C_{1-6}$ (e.g. $C_{1-3}$) alkyl or, preferably, hydrogen or aryl (e.g. phenyl; optionally substituted by one or more halo, e.g. chloro, atoms, so forming e.g. a chlorophenyl group), or, $R^x$ and $R^y$ are linked together to form a non-aromatic carbocyclic 3- to 6-membered spirocycle (preferably cyclopropyl), which ring is preferably unsubstituted;

both $R^x$ and $R^y$, when attached to the same carbon atom, preferably do not represent optionally substituted aryl;

when n represents 2, then $R^x$ and $R^y$ independently represent $C_{1-6}$ (e.g. $C_{1-3}$) alkyl or, preferably, hydrogen;

e.g. when Q represents a bond, n represents 1 or 2.

Most preferred groups that X may represent include —$CH_2$—, —$CH_2CH_2$—, —O—$CH_2CH_2$—, —N($CH_3$)—$CH_2CH_2$—, —S—$CH_2CH_2$—, 1,1-cyclopropyl and —C(H)(4-chlorophenyl)- (i.e. it is preferred that X is not a direct bond, but represents a group containing at least one linking atom).

Compounds of formula I that may be mentioned include those in which:

m and p independently represent 0 or 1;

when W represents —[$CR^xR^y$]$_m$— or —[$CR^xR^y$]$_p$—, then $R^x$ and $R^y$ independently represent $C_{1-6}$ alkyl or, preferably, hydrogen;

W represents a direct bond (i.e. m represents 0), —$CH_2$—, —C(O)— (i.e. p represents 0) or —C(O)$CH_2$—.

The $A_1$ to $A_5$-containing ring may be pyridyl (e.g. 2-pyridyl, 3-pyridyl, 4-pyridyl, 5-pyridyl or 6-pyridyl), but is preferably phenyl. The D ring is preferably pyridyl (e.g. 2-pyridyl, 3-pyridyl, 4-pyridyl, 5-pyridyl or 6-pyridyl) or, more preferably, phenyl. Each ring may be unsubstituted or substituted with one or two substituents defined herein (by $R^1$ to $R^6$, as appropriate). As stated herein, in a preferred embodiment of the invention, one of these rings is substituted with at least one substituent other than H as defined herein (by $R^1$ to $R^6$, as appropriate).

Most preferred compounds of formula I include those in which:

$A_1$ to $A_5$ respectively represent $C(R^1)$, $C(R^2)$, $C(R^3)$, $C(R^4)$ and $C(R^5)$;

D represents phenyl, pyridyl or pyrimidinyl optionally substituted by one or more $R^6$ groups;

$R^x$ and $R^y$, on each occasion when used herein, are independently selected from fluoro, preferably, H, $C_{1-6}$ alkyl (optionally substituted by one or more fluoro atoms), aryl (optionally substituted by one or more halo, e.g. chloro atoms) or $R^x$ and $R^y$ are linked to form, along with the carbon atom to which they are attached, a non-aromatic 3- to 8-membered ring (e.g. 3- to 6-membered ring), which ring is itself optionally substituted by one or more substituents selected from fluoro and/or $C_{1-6}$ (e.g. $C_{1-3}$, such as $C_{1-2}$) alkyl (optionally substituted by one or more fluoro atoms), but which 3- to 8- (e.g. 3- to 6-) membered ring is preferably unsubstituted (e.g. unsubstituted cyclopropyl);

$R^1$ to $R^5$ independently represent —CN, —N($R^{7a}$)$R^{7b}$, —N($R^7$)$_3^+$, —SR$^7$ or, preferably, H, halo (e.g. chloro or fluoro), —$R^7$, —CF$_3$, —C(O)—N($R^{7a}$)$R^{7b}$, —OR$^7$ or heteroaryl (e.g. a 5- or 6-membered heteroaryl group preferably containing one to three heteroatoms (preferably nitrogen heteroatoms), and which heteroaryl group is optionally substituted by one or more groups selected from $R^{16}$ and, preferably halo, e.g. chloro);

$R^6$ independently represents, on each occasion when used herein, —NO$_2$, —NR$^9$R$^{10}$, —SR$^{11}$, or, preferably, cyano, halo, —$R^8$ or —OR$^8$;

$R^7$, on each occasion when used herein, is selected from H and $C_{1-6}$ (e.g. $C_{1-3}$) alkyl (e.g. methyl) optionally substituted by one or more fluoro atoms (so forming for example a —CHF$_2$ or, preferably a —CF$_3$ group);

$R^{7a}$ and $R^{7b}$ are independently selected from H and $C_{1-6}$ (e.g. $C_{1-3}$) alkyl (e.g. methyl) optionally substituted by one or more fluoro atoms (so forming for example a —CHF$_2$ or, preferably a —CF$_3$ group); or $R^{7a}$ and $R^{7b}$ are optionally linked to form, along with the nitrogen atom to which they are attached, an aromatic or non-aromatic 3- to 6-membered ring (preferably an aromatic 5- or 6-membered ring), optionally containing 1 to 3 heteroatoms selected from O, S and N (preferably N heteroatoms), which ring is itself optionally substituted by one or more substituents selected from fluoro, —$R^7$ and =O; $R^a$, $R^8$, $R^9$, $R^{10}$, $R^{11}$, $R^{12}$, $R^{13}$, $R^{14}$, $R^{15a}$, $R^{15b}$, $R^{15c}$ and $R^{15d}$, on each occasion where used herein, independently represent H or $R^{16}$ (but $R^a$ and $R^8$ more preferably represent $R^{16}$); $R^{16}$ represents, on each occasion when used herein, $C_{1-6}$ ($C_{1-3}$) alkyl optionally substituted by one or more fluoro atoms (so forming for example a —CHF$_2$ or, preferably a —CF$_3$ group).

Further compounds of formula I that may be mentioned include those in which:

at least one of $R^1$ to $R^5$, when present, represents halo, —$R^7$, —CF$_3$, —CN, —C(O)$R^7$, —C(O)OR$^7$, —C(O)—N($R^{7a}$)$R^{7b}$, —N($R^7$)$_3^+$, —SR$^7$, —OR$^7$ or —NH(O)$R^7$, or any two of $R^1$ to $R^5$ which are adjacent to each other are optionally linked to form, along with two atoms of the essential benzene ring in the compound of formula I, an aromatic or non-aromatic 3- to 8-membered ring, optionally containing 1 to 3 heteroatoms selected from O, S and N, which ring is itself optionally substituted by one or more substituents selected from halo, —$R^7$, —OR$^7$ and =O.

Further compounds of formula I that may be mentioned include those in which:

at least one of $R^1$ to $R^5$, when present, represents heteroaryl, —OR$^7$, halo, —CF$_3$, —CN, —C(O)$R^7$, —C(O)—N($R^{7a}$)$R^{7b}$, —C(O)OR$^7$, —N($R^7$)$_3^+$ or —NH(O)$R^7$, or any two of $R^1$ to $R^5$ which are adjacent to each other are optionally linked to form, along with two atoms of the essential benzene ring in the compound of formula I, an aromatic or non-aromatic 3- to 8-membered ring selected from 2,3-dihydrobenzo[1,4]dioxinyl or tetrahydroquinolinyl, which may optionally be substituted by one or more halo atoms.

Further compounds of formula I that may be mentioned include those in which:

at least one of $R^1$ to $R^5$, when present, represents heteroaryl, —OR$^7$, halo, —CF$_3$, —CN, —C(O)$R^7$, —C(O)OR$^7$, —C(O)—N($R^{7a}$)$R^{7b}$, —N($R^7$)$_3^+$ or —NH(O)$R^7$.

Yet further compounds of formula I that may be mentioned include those in which:

at least one of $R^1$ to $R^5$, when present, represents 4H-[1,2,4]-triazolyl, —OR$^7$ (e.g. —OCH$_3$, or more preferably, —OCHF$_2$ or —OCF$_3$), or, more preferably, —Cl, —F, —CF$_3$, —CN or —C(O)—N($R^{7a}$)$R^{7b}$.

Yet further compounds of formula I that may be mentioned include those in which: at least one of $R^1$ to $R^5$, when present, represents —OR$^7$ or, more preferably, —Cl, —F, —CF$_3$, —CN or —C(O)—N($R^{7a}$)$R^{7b}$.

Compounds of formula I that may be mentioned include those in which:

$R^6$ independently represents —C(O)NR$^{15a}$R$^{15b}$ or, more preferably, cyano, —NO$_2$, —Br, —Cl, —F, —$R^8$, —OR$^8$, —NR$^9$R$^{10}$, —SR$^{11}$, —C(O)OR$^{13}$, —C(O)$R^{14}$, —S(O)$_2$NR$^{15c}$R$^{15d}$, aryl or heteroaryl (which aryl and heteroaryl groups are themselves optionally and independently substituted by one or more groups selected from halo and $R^{16}$), or any two $R^6$ groups which are adjacent to each other are optionally linked to form, along with two atoms of the essential benzene ring in the compound of formula I, quinoline, tetrahydroquinoline, isoquinoline or tetrahydroisoquinoline, wherein the additional ring system of the quinoline, tetrahydroquinoline, isoquinoline or tetrahydroisoquinoline moiety is itself optionally substituted by one or more substituents selected from halo, —$R^7$, —OR$^7$ and =O.

Further compounds of formula I that may be mentioned include those in which:

$R^6$ independently represents —C(O)NR$^{15a}$R$^{15b}$ or, more preferably, —$R^8$ or yet more preferably, cyano, —NO$_2$, —Br, —Cl, —F, —OR$^8$, —NR$^9$R$^{10}$, —SR$^{11}$, —C(O)OR$^{13}$, —C(O)$R^{14}$, —S(O)$_2$NR$^{15c}$R$^{15d}$, aryl or heteroaryl (which aryl and heteroaryl groups are themselves optionally and independently substituted by one or more groups selected from halo and $R^{16}$).

Yet further compounds of formula I that may be mentioned include those in which:

$R^6$ independently represents —C(O)NR$^{15a}$R$^{15b}$, —$R^8$, or, more preferably, —CN, —NO$_2$, —Br, —Cl, —F, —OR$^8$, —NR$^9$R$^{10}$, —SR$^{11}$, —C(O)OR$^{13}$ or —C(O)$R^{14}$.

Yet further compounds of formula I that may be mentioned include those in which:

$R^6$ independently represents —$R^8$ or, more preferably, —CN, —OCF$_3$, —NO$_2$, —Br, —Cl, —F, —OR$^8$, —NR$^9$R$^{10}$ or —SR$^{11}$.

Yet further compounds of formula I that may be mentioned include those in which:

$R^6$ independently represents —CN, —CF$_3$, —OCF$_3$, —F or, most preferably —Cl.

Compounds of formula I that may be mentioned include those in which:
n represents 2 or, more preferably, 1.
Further compounds of formula I that may be mentioned include those in which:
m represents 1 or, more preferably, 0;
p represents 1 or, more preferably, 0.
Further compounds of formula I that may be mentioned include those in which:
$A_5$ represents N or, more preferably, C(Cl) or C(H).
Further compounds of formula I that may be mentioned include those in which:
$A_1$ and $A_3$ independently represent N or, more preferably, C(H).
Further compounds of formula I that may be mentioned include those in which:
$A_2$ represents $C(R^2)$;
$A_1$ and $A_3$ to $A_5$ independently represent C(H) or N.
Yet further compounds of formula I that may be mentioned include those in which:
$A_2$ represents $C(R^2)$;
$R^2$ represents —$CF_3$;
$A_1$ and $A_3$ to $A_5$ independently represent C(H).
Further compounds of formula I that may be mentioned include those in which:
$A_5$ represents $C(R^5)$;
$A_1$ to $A_4$ independently represent C(H) or N.
Yet further compounds of formula I that may be mentioned include those in which:
$A_5$ represents $C(R^5)$;
$R^5$ represents —Cl;
$A_1$ to $A_4$ independently represent C(H).
Compounds of formula I that may be mentioned include those in which:
D represents (ortho-,para-)dichlorophenyl.
Compounds of formula I that may be mentioned include those in which:
D represents para-chlorophenyl.
More preferred compounds of formula I include those of the examples described hereinafter.
Preferred compounds of formula I include:
i) 5-(3,4-dichlorophenyl)imino-4-[[3-(trifluoromethyl)phenyl]methyl]-1,2,4-thiadiazolidin-3-one;
ii) 5-(3,4-dichlorophenyl)imino-4-[(4-methoxyphenyl)methyl]-1,2,4-thiadiazolidin-3-one;
iii) 4-[(4-chlorophenyl)methyl]-5-(3,4-dichlorophenyl)imino-1,2,4-thiadiazolidin-3-one;
iv) 5-(3,4-dichlorophenyl)imino-4-[(3,4-difluorophenyl)methyl]-1,2,4-thiadiazolidin-3-one;
v) 5-(3,4-dichlorophenyl)imino-4-[(3-fluorophenyl)methyl]-1,2,4-thiadiazolidin-3-one;
vi) 5-(3,4-dichlorophenyl)imino-4-[phenyl)methyl]-1,2,4-thiadiazolidin-3-one;
vii) 5-(3,4-dichlorophenyl)imino-4-phenethyl-1,2,4-thiadiazolidin-3-one;
viii) 4-[2-[(4-chlorophenyl)-methyl-amino]ethyl]-5-(3,4-dichlorophenyl)imino-1,2,4-thiadiazolidin-3-one;
ix) 4-[2-(4-chlorophenyl)sulfanylethyl]-5-(3,4-dichlorophenyl)imino-1,2,4-thiadiazolidin-3-one;
x) 3-[[(5-(3,4-dichlorophenyl)imino-3-oxo-1,2,4-thiadiazolidin-4-yl]methyl]-N-methylbenzamide;
xi) 5-[(6-chloro-3-pyridyl)imino]-4-[(3,4-difluorophenyl)methyl]-1,2,4-thiadiazolidin-3-one;
xii) 4-[[4-[(3,4-difluorophenyl)methyl]-3-oxo-1,2,4-thiadiazolidin-5-ylidene]amino]benzonitrile;
xiii) 4-[(3,4-difluorophenyl)methyl]-5-[4-(trifluoromethyl)phenyl]imino-1,2,4-thiadiazolidin-3-one;
xiv) 4-[(3,4-difluorophenyl)methyl]-5-[4-(trifluoromethoxy)phenyl]imino-1,2,4-thiadiazolidin-3-one;
xv) 3-[5-(3,4-dichlorophenyl)imino-3-oxo-1,2,4-thiadiazolidin-4-yl]methyl]benzonitrile;
xvi) 5-(3,4-dichlorophenyl)imino-4-[[4-(1,2,4-triazol-1-yl)phenyl]methyl]-1,2,4-thiadiazolidin-3-one;
xvii) 4-[1-(4-chlorophenyl)cyclopropyl]-5-(4-chlorophenyl)imino-1,2,4-thiadiazolidin-3-one;
xviii) 5-[(4-chlorophenyl)methylimino]-4-[(3,4-difluorophenyl)methyl]-1,2,4-thiadiazolidin-3-one;
N-[3-oxo-2-[[3-(trifluoromethyl)phenyl]methyl]-1,2,4-thiadiazol-5-yl]benzamide;
xix) 4-fluoro-N-[3-oxo-2-[[3-(trifluoromethyl)phenyl]methyl]-1,2,4-thiadiazol-5-yl]benzamide;
xx) 2-(4-fluorophenyl)-N-[3-oxo-2-[[3-(trifluoromethyl)phenyl]methyl]-1,2,4-thiadiazol-5-yl]acetamide;
xxi) 4-chloro-N-[2-[(3,4-difluorophenyl)methyl]-3-oxo-1,2,4-thiadiazol-5-yl]benzamide;
xxii) 4-chloro-N-[2-[(4-fluorophenyl)methyl]-3-oxo-1,2,4-thiadiazol-5-yl]benzamide;
xxiii) 4-chloro-N-[2-[(4-chlorophenyl)methyl]-3-oxo-1,2,4-thiadiazol-5-yl]benzamide;
xxiv) 4-chloro-N-[2-[2-(phenoxy)ethyl]-3-oxo-1,2,4-thiadiazol-5-yl]benzamide;
xxv) 4-chloro-N-[2-[2-[(4-chlorophenyl)-methyl-amino]ethyl]-3-oxo-1,2,4-thiadiazol-5-yl]benzamide;
xxvi) 4-chloro-N-[2-[2-(4-chlorophenyl)sulfanylethyl]-3-oxo-1,2,4-thiadiazol-5-yl]benzamide;
xxvii) 3,4-dichloro-N-[2-[1-(4-fluorophenyl)cyclopropyl]-3-oxo-1,2,4-thiadiazol-5-yl]benzamide;
xxviii) 3,4-dichloro-N-[2-[(4-fluorophenyl)methyl]-3-oxo-1,2,4-thiadiazol-5-yl]benzamide;
xxix) N-[2-[(4-fluorophenyl)methyl]-3-oxo-1,2,4-thiadiazol-5-yl]-4-methoxy-benzamide;
xxx) 2,6-dichloro-N-[2-[(4-fluorophenyl)methyl]-3-oxo-1,2,4-thiadiazol-5-yl]benzamide;
xxxi) 2,4-dichloro-N-[2-[(4-fluorophenyl)methyl]-3-oxo-1,2,4-thiadiazol-5-yl]benzamide;
xxxii) N-[2-[(4-fluorophenyl)methyl]-3-oxo-1,2,4-thiadiazol-5-yl]-4-(trifluoromethoxy)-benzamide;
xxxiii) N-[2-[(4-fluorophenyl)methyl]-3-oxo-1,2,4-thiadiazol-5-yl]-3,5-bis(trifluoromethyl)-benzamide;
xxxiv) 3,4-difluoro-N-[2-[(4-fluorophenyl)methyl]-3-oxo-1,2,4-thiadiazol-5-yl]benzamide;
xxxv) 2-chloro-6-fluoro-N-[2-[(4-fluorophenyl)methyl]-3-oxo-1,2,4-thiadiazol-5-yl]benzamide;
xxxvi) 3,5-difluoro-N-[2-[(4-fluorophenyl)methyl]-3-oxo-1,2,4-thiadiazol-5-yl]benzamide;
xxxvii) 5-(3,4-dichlorophenyl)imino-4-(2-phenoxyethyl)-1,2,4-thiadiazolidin-3-one;
xxxviii) 5-(3,4-dichlorophenylamino)-2-(2-phenoxyethyl)-[1,2,4]thiadiazol-3-one;
xxxix) 4-benzhydryl-5-(3,4-dichlorophenyl)imino-1,2,4-thiadiazolidin-3-one;
xl) 4-chloro-N-[4-[(4-fluorophenyl)methyl]-3-oxo-1,2,4-thiadiazolidin-5-ylidene]benzamide;
xli) 4-chloro-N-[4-[(4-chlorophenyl)methyl]-3-oxo-1,2,4-thiadiazolidin-5-ylidene]benzamide;
xlii) 4-chloro-N-[3-oxo-4-[[3-(trifluoromethyl)phenyl]methyl]-1,2,4-thiadiazolidin-5-ylidene]-benzamide;
xliii) N-[4-[(3-fluorophenyl)methyl]-3-oxo-1,2,4-thiadiazolidin-5-ylidene]-4-(trifluoromethyl)-benzamide;
xliv) N-[4-[(3-fluorophenyl)methyl]-3-oxo-1,2,4-thiadiazolidin-5-ylidene]-3,5-bis(trifluoromethyl)benzamide;
xlv) N-[4-[(3,4-dichlorophenyl)methyl]-3-oxo-1,2,4-thiadiazolidin-5-ylidene]-3,4-difluorobenzamide;

xlvi) 1,5-(3,4-dichlorophenylamino)-2-(4-methoxybenzyl)-[1,2,4]thiadiazol-3-one;
xlvii) 1,5-(3,4-dichlorophenylamino)-2-(4-chlorobenzyl)-[1,2,4]thiadiazol-3-one;
xlviii) 1,5-(3,4-dichlorophenylamino)-2-(3,4-difluorobenzyl)-[1,2,4]thiadiazol-3-one;
xlix) 1,5-(3,4-dichlorophenylamino)-2-(3-fluorobenzyl)-[1,2,4]thiadiazol-3-one;
l) 1,5-(3,4-dichlorophenylamino)-2-(benzyl)-[1,2,4]thiadiazol-3-one;
li) 5-(3,4-dichlorophenylamino)-2-phenethyl-[1,2,4]thiadiazol-3-one;
lii) 2-[2-[(4-chlorophenyl)-methyl-amino]ethyl]-5-[(3,4-dichlorophenyl)amino]-1,2,4-thiadiazol-3-one;
liii) 2-[2-(4-chlorophenyl)sulfanylethyl]-5-[(3,4-dichlorophenyl)amino]-1,2,4-thiadiazol-3-one;
liv) 3-[[5-[(4-chlorophenyl)amino]-3-oxo-1,2,4-thiadiazol-2-yl]methyl]-N-methylbenzamide;
lv) 5-[(6-chloro-3-pyridyl)amino]-2-[(3,4-difluorophenyl)methyl]-1,2,4-thiadiazol-3-one;
lvi) 2-[(3,4-difluorophenyl)methyl]-5-[[4-(trifluoromethyl)phenyl]amino]-1,2,4-thiadiazol-3-one;
lvii) 2-[(3,4-difluorophenyl)methyl]-5-[[4-(trifluoromethoxy)phenyl]amino]-1,2,4-thiadiazol-3-one;
lviii) 5-[(4-chlorophenyl)amino]-2-[1-(4-chlorophenyl)cyclopropyl]-1,2,4-thiadiazol-3-one;
lix) 5-[(3,4-dichlorophenyl)methylamino]-2-[(3,4-difluorophenyl)methyl]-1,2,4-thiadiazol-3-one;
lx) 3,4-dichloro-N-[4-[(4-fluorophenyl)methyl]-3-oxo-1,2,4-thiadiazolidin-5-ylidene]benzamide;
lxi) 2-[(4-methoxyphenyl)methyl]-5-[[4-(trifluoromethyl)phenyl]amino]-1,2,4-thiadiazol-3-one;
lxii) 2-[(4-chlorophenyl)methyl]-5-[[4-(trifluoromethyl)phenyl]amino]-1,2,4-thiadiazol-3-one;
lxiii) 2-[(3-fluorophenyl)methyl]-5-[[4-(trifluoromethyl)phenyl]amino]-1,2,4-thiadiazol-3-one;
lxiv) 2-[phenylethyl]-5-[[4-(trifluoromethyl)phenyl]amino]-1,2,4-thiadiazol-3-one;
lxv) 2-[(4-methoxyphenyl)methyl]-5-[[4-(trifluoromethoxy)phenyl]amino]-1,2,4-thiadiazol-3-one;
lxvi) 2-[(4-chlorophenyl)methyl]-5-[[4-(trifluoromethoxy)phenyl]amino]-1,2,4-thiadiazol-3-one;
lxvii) 2-[(3-fluorophenyl)methyl]-5-[[4-(trifluoromethoxy)phenyl]amino]-1,2,4-thiadiazol-3-one;
lxviii) 2-[phenylethyl]-5-[[4-(trifluoromethoxy)phenyl]amino]-1,2,4-thiadiazol-3-one; and
lxix) 4-[[2-[(3,4-difluorophenyl)methyl]-3-oxo-1,2,4-thiadiazol-5-yl]amino]benzonitrile.

Compound names were derived using the commercially available software package Autonom (brand of nomenclature software provided as an add-on for use in the Symyx Draw 2.1™ office suite marketed by MDL Information Systems).

Throughout this specification, structures may or may not be presented with chemical names. Where any question arises as to nomenclature, the structure prevails. Where it is possible for a compound to exist as a tautomer the depicted structure represents one of the possible tautomeric forms, wherein the actual tautomeric form(s) observed may vary depending on environmental factors such as solvent, temperature or pH.

Compounds of formula I may be prepared in accordance with techniques that are well known to those skilled in the art, for example as described hereinafter.

According to a further embodiment of the invention there is provided a process for the preparation of a compound of formula I, which process comprises:

(i) for compounds of formula I wherein A represents S, cyclisation of a compound of formula IIa,

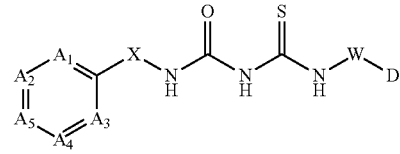

wherein $A_1$ to $A_5$, X, W and D are as hereinbefore defined, under reaction conditions known to those skilled in the art, for example in the presence of a suitable bromine source (e.g. N-bromo succinimide or bromine) and a suitable solvent (e.g. methanol, ethanol, ethyl acetate) and at a suitable temperature (e.g. −10° C. to 80° C.) as described in Castro et al. (*Bioorganic. Med. Chem.* 2008, 16, 495-510) or Kaugars et al. (*J. Org. Chem.* 1979, 44(22), 3840-3843), or in the presence of a suitable base (e.g. sodium hydroxide) in a suitable solvent (e.g. water containing hydrogen peroxide (e.g. a 30% $H_2O_2$ solution in water)) and at a suitable temperature (e.g. −10° C. to 100° C.) as described in Castro et al. (ibid), Cho et al. (*J. Heterocyclic Chem.* 1991, 28, 1645-1649) and Encinas et al. (*Eur. J. Org. Chem.* 2007, 5603-5608);

(ii) for compounds of formula I wherein A represents S, W represents —[$CR^xR^y$]$_m$— and m represents 1 or 2, reaction of a compound of formula III,

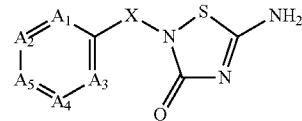

wherein $A_1$ to $A_5$ and X are as hereinbefore defined, with a compound of formula IV,

L$_2$-W$^1$-D        IV wherein $L_2$ represents a suitable leaving group such as halo (e.g. chloro), $W^1$ represents —[$CR^xR^y$]$_m$— in which m represents 1, and D is as hereinbefore defined, under reaction conditions known to those skilled in the art, for example in the presence of a suitable base (e.g. NaH, NaOH, triethylamine, pyridine, another suitable base mentioned at process step or mixtures thereof) and solvent (e.g. pyridine (which may serve as the base and solvent), DMF or dichloromethane (e.g. further in the presence of water and, optionally, a phase transfer catalyst)) for example at room temperature e.g. as described in Hurst, D. T.; Stacey, A. D., Nethercleft, M., Rahim, A., Harnden, M. R. *Aust. J. Chem.* 1998, 41, 1221;

(iii) for compounds of formula I wherein A represents S, W represents —[$CR^xR^y$]$_m$— and m represents 0, reaction of a compound of formula III as hereinbefore defined with a compound of formula V,

L$_3$-D        V wherein $L_3$ is a suitable leaving group (e.g. halo) and D is as hereinbefore defined, under reaction conditions known to those skilled in the art, for example in the presence of a suitable base (e.g. a tributyltin amine or cyclohexylamine and lithium bis(trimethylsilyl)amide), a suitable catalyst (e.g. PdCl$_2$(P(o-toluyl)$_3$)$_2$), a suitable solvent (e.g. toluene) and at a suitable temperature (e.g. from room temperature to 105° C.), e.g. as described in Harwig et al. *J. Am. Chem. Soc.* (1994), 116, 5969-5970, Buchwald et al. *J. Am. Chem. Soc.* (1994), 116, 7901-7902 and Buchwald et al. *Org. Process Res. Dev.* (2006) 10(4), 762-769;

(iv) for compounds of formula I wherein A represents S, W represents —C(O)—[CR$^x$R$^y$]$_p$—, reaction of a compound of formula III as hereinbefore defined, with a compound of formula VI,

L$_4$-W$^2$-D      VI wherein L$_4$ is a suitable leaving group (e.g. halo) or —OH, W$^2$ represents —C(O)—[CR$^x$R$^y$]$_p$—, and D is as hereinbefore defined, when L$_4$ represents a suitable leaving group, under reaction conditions known to those skilled in the art, for example in an appropriate solvent (e.g. toluene, xylenes, DCM, chloroform), optionally in the presence of an base (e.g. pyridine, Hunig's base, triethylamine) and at reduced to elevated temperatures (e.g. from 0° C. to 140° C.) or when L$_4$ represents OH, under standard coupling reaction conditions, for example, in the presence of a suitable coupling reagent (e.g. 1,1'-carbonyldiimidazole, N,N-dicyclohexyl-carbodiimide, 1-(3-dimethylamino-propyl)-3-ethylcarbodiimide (or hydrochloride thereof), N,N'-disuccinimidyl carbonate, benzotriazol-1-yloxytris(dimethylamino)-phosphonium hexafluorophosphate, 2-(1H-benzotriazol-1-yl)-1,1,3,3-tetramethyluronium hexafluorophosphate, benzotriazol-1-yloxytris-pyrrolidinophosphonium hexafluorophosphate, bromo-tris-pyrrolidinophosponium hexafluoro-phosphate, 2-(1H-benzotriazol-1-yl)-1,1,3,3-tetramethyluronium tetra-fluorocarbonate) or 1-cyclohexyl-carbodiimide-3-propyloxymethyl polystyrene, optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)-amide, sodium bis(trimethylsilyl) amide, potassium tert-butoxide, lithium diisopropylamide, lithium 2,2,6,6-tetramethylpiperidine or mixtures thereof) and an appropriate solvent (e.g. tetrahydrofuran, pyridine, toluene, dichloromethane, chloroform, acetonitrile or dimethylformamide) and at reduced to elevated temperatures (e.g. from 0° C. to 140° C.);

(v) for compounds of formula I wherein A represents S, Q is a bond and n is 0, 1 or 2, or Q is —O— or —S— and n is 1 or 2, reaction of a compound of formula VII,

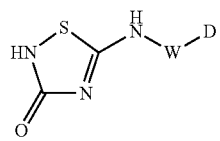
VII wherein W and D are as hereinbefore defined, with a compound of formula VIII,

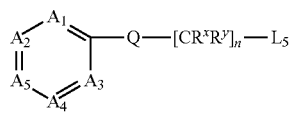
VIII

Wherein a$_1$ to a$_5$, r$^x$ and r$^y$ are as hereinbefore defined, l$_5$ is a suitable leaving group (e.g. Bromo, chloro, iodo) and either q is a bond and n is 0, 1 or 2, or q is -o- or -s- and n is 1 or 2, under reaction conditions known to those skilled in the art, for example in the presence of a suitable base (e.g. Nah, naoh, triethylamine, pyridine) and solvent (e.g. Pyridine (which may serve as the base and solvent) dmf or dichloromethane (e.g. Further in the presence of water and, optionally, a phase transfer catalyst)), for example at room temperature e.g. As described in hurst, d. T.; stacey, a. D., nethercleft, m., rahim, a., harnden, m. R. *Aust. J. Chem.* 1998, 41, 1221;

(vi) for compounds of formula I wherein A represents S and W is —[CR$^x$R$^y$]$_m$—, reaction of a compound of formula IX,

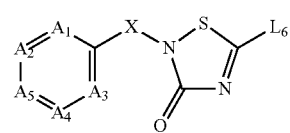
IX wherein L$_6$ represents a suitable leaving group (e.g. halo) and A$_1$ to A$_5$ and X are as hereinbefore defined, with a compound of formula X,

H$_2$N—W-D      X wherein W and D$_1$ to D$_5$ are as hereinbefore defined, under reaction conditions known to those skilled in the art, for example those described by Keilen et al (Acta Chemica Scandinavica 1988, B 42, 363-366), e.g. in a suitable solvent (e.g. chloroform, methylenechloride), in the presence of a suitable base (e.g. Hunig's base, triethyl amine) and at a suitable temperature (e.g. room temperature to 150° C., such as less than <100° C.); and (vii) for compounds of formula I wherein B represents S, cyclisation of a compound of formula IIa,

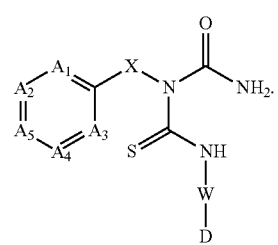
IIb

Compounds of formula IIa may be prepared by reaction of a compound of formula XI,

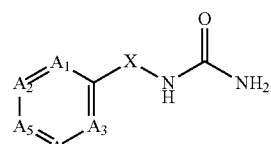
XI wherein A$_1$ to A$_5$ and X are as hereinbefore defined, with a compound of formula XII,

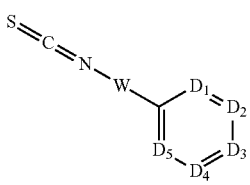

XII wherein W and $D_1$ to $D_5$ are as hereinbefore defined, under reaction conditions known to those skilled in the art, for example in a suitable solvent (e.g. acetone, dimethylformamide or 20% dimethylformamide in acetonitrile) at a suitable temperature (e.g. from –10° C. to 50° C.) and in the absence of a base, e.g. as described in Castro et al. (*Bioorganic. Med. Chem.* 2008, 16, 495-510) or Kaugars et al. (*J. Org. Chem.* 1979, 44(22), 3840-3843). Alternatively, a compound of formula I may be formed directly by allowing any product so formed to be directly treated under reaction conditions such as those described hereinbefore (e.g. process step (i) above).

Compounds of formula IIb may be prepared by reaction of a compound of formula XI as hereinbefore described, with a compound of formula XII under reaction conditions known to those skilled in the art, for example in a suitable solvent (e.g. acetone, dimethylformamide) at a suitable temperature (e.g. from –10° C. to 50° C.) and in the presence of a suitable base (e.g. n-butyl lithium), e.g. as described in Castro et al. (*Bioorganic. Med. Chem.* 2008, 16, 495-510) or Kaugars et al. (*J. Org. Chem.* 1979, 44(22), 3840-3843). Alternatively, a compound of formula I may be formed directly by allowing any product so formed to be directly treated under reaction conditions such as those described hereinbefore (e.g. process step (vii) above).

Alternatively, compounds of formula IIb may be formed by the selective N-alkylation of N-(3-oxo-1,2,4-thiadiazolidin-5-ylidene)amide derivates as described by Castro et al (Bioorganic. Med. Chem. 2008, 16, 495-510).

Compounds of formula IX may be prepared by reaction of a compound of formula III with $NaNO_2$ and a suitable halogen source (e.g. hydrochloric acid), under reaction conditions known to those skilled in the art, for example such as those described in Foroumadi et al. (1999) *Arzneim. Forsch.* 49, 1035-1038 or Foroumadi et al. (2005) *Arch. Pharm. Chem. Life Sci.* 338, 112-116, for example in the presence of a suitable metal (e.g. copper powder).

Compounds of formula XI may be prepared by analogy to the methods described in Xu et al. (*Tetrahedron Lett.* 1998, 39, 1107-1110) and Katritsky et al. (*ARKIVOC (Archive for Organic Chemistry)* 2003 (viii) 8-14).

For compounds of formula XII in which W represents —C(O)—, reaction of a compound of formula XIII,

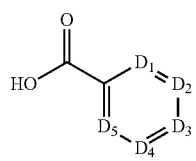

XIII or the corresponding acyl halide (e.g. acyl chloride), or derivative thereof, wherein $D_1$ to $D_5$ are as hereinbefore defined, with a thiocyanate (e.g. an alkali metal thiocyanate, such as potassium thiocyanate), under reaction conditions known to those skilled in the art, for example in the presence of a suitable solvent (such as acetone), as described in Cho et al, *J. Heterocyclic Chem.* 1991, 28, 1645-1649).

Compounds of formulae III, IV, V, VI, VII, VIII, X and XIII are either commercially available, are known in the literature, or may be obtained either by analogy with the processes described herein (or processes described in references contained herein), or by conventional synthetic procedures, in accordance with standard techniques, from available starting materials using appropriate reagents and reaction conditions.

Substituents, such as $R^2$, $R^3$ and $R^4$ in final compounds of formula I (or precursors thereto and other relevant intermediates) may be modified one or more times, after or during the processes described above by way of methods that are well known to those skilled in the art. Examples of such methods include substitutions, reductions (e.g. carbonyl bond reductions in the presence of suitable and, if necessary, chemoselective, reducing agents such as $LiBH_4$ or $NaBH_4$), oxidations, alkylations, acylations, hydrolyses, esterifications, and etherifications. The precursor groups can be changed to a different such group, or to the groups defined in formula I, at any time during the reaction sequence.

Compounds of formula I may be isolated from their reaction mixtures using conventional techniques.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3rd edition, T. W. Greene & P. G. M. Wutz, Wiley-Interscience (1999).

As used herein, the term "functional groups" means, in the case of unprotected functional groups, hydroxy-, thiolo-, aminofunction, carboxylic acid and, in the case of protected functional groups, lower alkoxy, N-, O-, S-acetyl, carboxylic acid ester.

Medical and Pharmaceutical Uses

Compounds of formula I are indicated as pharmaceuticals. According to a further embodiment of the invention there is provided a compound of formula I, or a pharmaceutically-acceptable salt or solvate, or a pharmaceutically functional derivative thereof, for use as a pharmaceutical.

Advantageously, compounds of formula I may be AMPK agonists, i.e. they may activate AMPK. By 'activate AMPK', we mean that the steady state level of phosphorylation of the Thr-172 moiety of the AMPK-α subunit is increased compared to the steady state level of phosphorylation in the absence of the agonist. Alternatively, or in addition, we mean that there is a higher steady state level of phosphorylation of any other proteins downstream of AMPK, such as acetyl-CoA carboxylase (ACC).

As the compounds of formula I may be AMPK activators, they may therefore be useful in the treatment of diseases such as those described herein, especially cancer.

Compounds of formula I may reduce the rate of cell proliferation when tested in an assay using a human breast cancer cell line (e.g. MDA-MB-231). The compounds may thus possess a beneficial inhibitory effect on the ability of tumors of this type, and of cancers generally, to survive. Compounds of formula I may also reduce the rate of cell proliferation when tested in other cancer cells lines (e.g. any p53 mutant or p53 null cell line) such as, but not limited to, MCF-7, PC-3, Jurkat, SK-OV-3, HL60, MV4-11, HT-29, K562, MDA-MB-231, HCT116 wt, A-549, DU-145, LOVO, HCT-116 and PANC-1, independent of p53 status.

Compounds of formula I are therefore indicated for the inhibition of cell proliferation. Compounds of formula I are therefore indicated for use in the treatment of cancer.

According to a further embodiment of the invention, there is provided the use of a compound of formula I, or a pharmaceutically-acceptable salt or solvate, or a pharmaceutically functional derivative thereof for the manufacture of a medicament for the treatment of cancer.

The compounds of formula I may be useful in the treatment of both primary and metastatic cancers.

The term "cancer" will be understood by those skilled in the art to include one or more diseases in the class of disorders that is characterized by uncontrolled division of cells and the ability of these cells to invade other tissues, either by direct growth into adjacent tissue through invasion, proliferation or by implantation into distant sites by metastasis.

In a preferred embodiment, compounds of formula I are capable of inhibiting the proliferation of cancer cells. By "proliferation" we include an increase in the number and/or size of cancer cells.

Alternatively, or preferably in addition, compounds of formula I are capable of inhibiting metastasis of cancer cells.

By "metastasis" we mean the movement or migration (e.g. invasiveness) of cancer cells from a primary tumor site in the body of a subject to one or more other areas within the subject's body (where the cells can then form secondary tumors). Thus, in one embodiment the invention provides compounds and methods for inhibiting, in whole or in part, the formation of secondary tumors in a subject with cancer. It will be appreciated by skilled persons that the effect of a compound of formula I on "metastasis" is distinct from any effect such a compound may or may not have on cancer cell proliferation.

Advantageously, compounds of formula I may be capable of inhibiting the proliferation and/or metastasis of cancer cells selectively.

By "selectively" we mean that the combination product inhibits the proliferation and/or metastasis of cancer cells to a greater extent than it modulates the function (e.g. proliferation) of non-cancer cells. Preferably, the compound inhibits the proliferation and/or metastasis of cancer cells only.

Compounds of formula I may be suitable for use in the treatment of any cancer type, including all tumors (non-solid and, preferably, solid tumors, such as carcinoma, adenoma, adenocarcinoma, blood cancer, irrespective of the organ). For example, the cancer cells may be selected from the group consisting of cancer cells of the breast, bile duct, brain, colon, stomach, reproductive organs, thyroid, hematopoietic system, lung and airways, skin, gallbladder, liver, nasopharynx, nerve cells, kidney, prostate, lymph glands and gastrointestinal tract. Preferably, the cancer is selected from the group of colon cancer (including colorectal adenomas), breast cancer (e.g. postmenopausal breast cancer), endometrial cancer, cancers of the hematopoietic system (e.g. leukemia, lymphoma, etc), thyroid cancer, kidney cancer, oesophageal adenocarcinoma, ovarian cancer, prostate cancer, pancreatic cancer, gallbladder cancer, liver cancer and cervical cancer. More preferably, the cancer is selected from the group of colon, prostate and, particularly, breast cancer. Where the cancer is a non-solid tumor, it is preferably a hematopoietic tumor such as a leukemia (e.g. Acute Myelogenous Leukemia (AML), Chronic Myelogenous Leukemia (CML), Acute Lymphocytic Leukemia (ALL), Chronic Lymphocytic Leukemia (CLL).

Preferably, the cancer cells are breast cancer cells.

According to a further embodiment of the invention there is provided a method of treatment of cancer, which method comprises the administration of an effective amount of a compound of formula I, or a pharmaceutically-acceptable salt or solvate, or a pharmaceutically functional derivative thereof, to a patient in need of such treatment.

Compounds of formula I may also be of use in the treatment of a disorder or condition ameliorated by the activation of AMPK.

Compounds of formula I may be suitable for use in the treatment of side-effects caused by cancer (e.g. cachexia).

According to a further embodiment of the invention, there is provided the use of a compound of formula I, or a pharmaceutically-acceptable salt or solvate, or a pharmaceutically functional derivative thereof, for the manufacture of a medicament for the treatment of a disorder or condition ameliorated by the activation of AMPK.

The terms "disorder or condition ameliorated by the activation of AMPK" will be understood by those skilled in the art to include, in addition to cancer, diabetes, hyperinsulinemia and associated conditions, a condition/disorder where fibrosis plays a role, sexual dysfunction, osteoporosis and neurodegenerative diseases.

Compounds of formula I may thus also be indicated for use in the treatment of a disorder or a condition caused by, linked to, or contributed to by, hyperinsulinemia.

The terms "disorder or condition caused by, linked to, or contributed to by, hyperinsulinemia" or "treatment of hyperinsulinemia or an associated condition" will be understood by those skilled in the art to include hyperinsulinemia and associated conditions, such as type 2 diabetes, glucose intolerance, insulin resistance, metabolic syndrome, dyslipidemia, hyperinsulinism in childhood, hypercholesterolemia, high blood pressure, obesity, fatty liver conditions, diabetic nephropathy, diabetic neuropathy, diabetic retinopathy, cardiovascular disease, atherosclerosis, cerebrovascular conditions such as stroke, systemic lupus erythematosus, neurodegenerative diseases such as Alzheimer's disease, and polycystic ovary syndrome. Other disease states include progressive renal disease such as chronic renal failure. Preferred disorders include hyperinsulinemia and, particularly, type 2 diabetes.

Certain compounds of formula I may also have the additional advantage that they exhibit partial agonist activity and may therefore be useful in conditions, such as late type 2 diabetes, in which stimulation of the production of insulin is required. By "agonist activity", we include direct and indirect-acting agonists.

According to a further embodiment of the invention there is provided a method of treatment of a disorder or condition ameliorated by the activation of AMPK, which method comprises the administration of an effective amount of a compound of formula I, or a pharmaceutically-acceptable salt or solvate, or a pharmaceutically functional derivative thereof, to a patient in need of such treatment. An effective amount can be determined by a physician and will be determined for a specific patient by assessment of the patient's clinical parameters including, but not limited to the stage of disease, age, gender and histology.

Compounds of formula I may thus also be of use in the treatment of a condition/disorder where fibrosis plays a role. Compounds of formula I may also be useful in the treatment of sexual dysfunction (e.g. the treatment of erectile dysfunction).

A condition/disorder where fibrosis plays a role includes (but is not limited to) scar healing, keloids, scleroderma, pulmonary fibrosis (including idiopathic pulmonary fibrosis), nephrogenic systemic fibrosis, and cardiovascular fibrosis (including endomyocardial fibrosis), systemic sclerosis, liver cirrhosis, eye macular degeneration, retinal and vitreal retinopathy, Crohn's/inflammatory bowel disease, post surgical scar tissue formation, radiation and chemotherapeutic-drug induced fibrosis, and cardiovascular fibrosis.

Compounds of formula I may thus also be of use in the treatment of osteoporosis.

Compounds of formula I may thus also be of use in the treatment of inflammation.

Compounds of formula I may thus also be of use in the treatment of sexual dysfunction.

Compounds of formula I may thus also be of use in the treatment of heart failure.

Compounds of formula I may thus also be of use in the treatment of neurodegenerative diseases (e.g. Alzheimer's disease, Parkinson's disease and Huntington's disease, amyotrophic lateral sclerosis, polyglutamine disorders, such as spinal and bulbar muscular atrophy (SBMA), dentatorubral and pallidoluysian atrophy (DRPLA), and a number of spinocerebellar ataxias (SCA)).

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, the relevant disease states.

"Patients" include mammalian (including human) patients.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

In accordance with the invention, compounds of formula I may be administered alone, but are preferably administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Preferred modes of delivery include oral, intravenous, cutaneous or subcutaneous, nasal, intramuscular, or intraperitoneal delivery.

Compounds of formula I will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* 249, 1527 (1990).

Otherwise, the preparation of suitable formulations may be achieved non-inventively by the skilled person using routine techniques and/or in accordance with standard and/or accepted pharmaceutical practice.

Another aspect of the present invention includes a pharmaceutical composition comprising a therapeutically effective amount of a compound of formula I, or a pharmaceutically-acceptable salt or solvate, or a pharmaceutically functional derivative thereof, in combination with a pharmaceutically acceptable excipient, such as an adjuvant, diluent or carrier.

The amount of compound of formula I in the formulation will depend on the severity of the condition, and on the patient, to be treated, as well as the compound(s) which is/are employed, but may be determined non-inventively by the skilled person.

Depending on the disorder, and the patient, to be treated, as well as the route of administration, compounds of formula I may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I (or, if employed, a corresponding amount of a pharmaceutically acceptable salt or prodrug thereof).

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

The compounds of formula I may be used or administered in combination with one or more additional drugs useful in the treatment of cancer, in combination therapy.

According to a further embodiment of the invention, there is provided a combination product comprising:

(A) a compound of formula I; and
(B) another therapeutic agent useful in the treatment of cancer,
wherein each of components (A) and (B) is formulated in admixture with a pharmaceutically-acceptable adjuvant, diluent or carrier.

Other therapeutic agents useful in the treatment of cancer include standard cancer therapies, such as cytostatica, irradiation and photodynamic therapy, among others known to the physician.

It is preferred that the other therapeutic agent is a cytostatic (such as a taxane (e.g. docetaxel and, particularly, paclitaxel) or preferably, a platin (e.g. cisplatin and carboplatin) or an anthracycline (e.g. doxorubicin)) or an angiogenesis inhibitor, or a pharmaceutically-acceptable salt, solvate or pharmaceutically functional derivative of either of these. However, the other therapeutic agent may also be selected from:

(i) tamoxifen, or a pharmaceutically-acceptable salt, solvate or pharmaceutically functional derivative thereof;
(ii) an aromatase inhibitor (i.e. a compound that blocks the production of estrogen from adrenal androgens via the aromatase pathway in peripheral tissues), or a pharmaceutically-acceptable salt, solvate or pharmaceutically functional derivative thereof. Preferred AIs include anastrozole, letrozole and exemastane;
(iii) trastuzumab (Herceptin), or another antibody that is useful in the treatment of cancer, such as bevacizumab, cetuximab or panitumumab;
(iv) a tyrosine kinase inhibitor (i.e. a compound that blocks (or is capable of blocking), to a measurable degree, the autophosphorylation of tyrosine residues, thereby preventing activation of the intracellular signalling pathways in tumor cells), or a pharmaceutically-acceptable salt, solvate or pharmaceutically functional derivative thereof. Preferred TKIs include inhibitors of the vascular endothelial growth factor (VEGF) family, and/or the HER-family of TKs, such as HER-1/Human Epidermal Growth Factor (EGFR; erbB1), HER3 (erbB3), HER4 (erbB4) and, more particularly, HER2 (erbB2). Preferred TKIs thus include imatinib, gefitinib, erlotinib, canertinib, sunitinib, zactima, vatalanib, sorafenib, leflunomide and, particularly, lapatinib;
(v) a glitazone, such as troglitazone, pioglitazone and rosiglitazone, or a pharmaceutically-acceptable salt, solvate or pharmaceutically functional derivative thereof;
(vi) a biguanide such as phenformin, buformin, or, most preferably, metformin, or a pharmaceutically-acceptable salt, solvate or pharmaceutically functional derivative thereof;
(vii) a statin, such as fluvastatin, simvastatin, rosuvastatin, pravastatin, atorvastatin and, particularly, lovastatin, or a pharmaceutically-acceptable salt, solvate or pharmaceutically functional derivative thereof;
(viii) an inhibitor of activity of the mammalian target of rapamycin (mTOR), such as rapamycin, or a pharmaceutically-acceptable salt, solvate or pharmaceutically functional derivative thereof;
(ix) an oligomycin, such as oligomycin A, oligomycin B, oligomycin C, oligomycin D (rutamycin A), oligomycin E, oligomycin F, rutamycin B, 44-homooligomycin A and 44-homooligomycin B, or a pharmaceutically-acceptable salt, solvate or pharmaceutically functional derivative thereof;
(x) AICAR (aminoimidazole carboxamide ribonucleotide), or a pharmaceutically-acceptable salt, solvate or pharmaceutically functional derivative thereof;
(xi) a peroxisome proliferator-activated receptor (PPAR) agonist (which also include thiazolidinediones), or a pharmaceutically-acceptable salt, solvate or pharmaceutically functional derivative thereof;
(xii) A-769662, or a pharmaceutically-acceptable salt, solvate or pharmaceutically functional derivative thereof;
(xiii) D942 (5-(3-(4-(2-(4-Fluorophenyl)ethoxy)-phenyl)propyl)furan-2-carboxylic acid), or a pharmaceutically-acceptable salt, solvate or pharmaceutically functional derivative thereof;
(xiv) AM251 (a $CB_1$ receptor antagonist), or a pharmaceutically-acceptable salt, solvate or pharmaceutically functional derivative thereof;
(xv) a SIRT1 activator, such as resveratrol and SRT-1720 (N-[2-[3-(piperazin-1-ylmethyl)imidazo[2,1-b][1,3]thiazol-6-yl]phenyl]quinoxal-ine-2-carboxamide), or a pharmaceutically-acceptable salt, solvate or pharmaceutically functional derivative thereof; and/or
(xvi) salidroside, or a pharmaceutically-acceptable salt, solvate or pharmaceutically functional derivative thereof.

By "agonist" we include direct and indirect-acting agonists.

It has recently been suggested in the literature (see, for example, *Mol. Cancer Ther.*, 5, 430 (2006), *Cancer Res.*, 66, 10269 (2006) and *Int. J. Cancer*, 118, 773 (2006)) that the above mentioned compound classes (v) to (vii) may be used in the treatment of cancer, as described herein.

When the other therapeutic agent is (particularly) in category (i) or (ii) above, combination products according to embodiments of the invention are particularly useful in the treatment of ER-positive cancers and/or early-stage breast cancers, for example in adjuvant therapy (i.e. reducing the risk of the cancer coming back after surgery), in neo-adjuvant therapy (before surgery, to shrink a large breast cancer so that a lumpectomy is possible), in the control of breast cancers that have come back after initial treatment, or in the control of breast cancers that cannot be removed when first diagnosed. Such combination products according to embodiments of the invention are also particularly useful in the treatment of patients at a high risk of breast cancer.

When the other therapeutic agent is (particularly) in category (iii) or (iv) above, combination products according to embodiments of the invention are particularly useful in the treatment of HER2-positive cancers.

Pharmaceutically-acceptable salts, solvates or pharmaceutically functional derivatives of any of the compounds listed in categories (i), (ii) and (iv) to (xvi) above are as described hereinbefore. In particular, when the other therapeutic agent is tamoxifen, preferred pharmaceutically-acceptable salts include those of citric acid, when the other therapeutic agent is imatinib, preferred pharmaceutically-acceptable salts include mesylate salts and when the other therapeutic agent is sunitinib, preferred pharmaceutically-acceptable salts include maleate salts.

Combination products as described herein provide for the administration of compound of formula I in conjunction with the other therapeutic agent, and may thus be presented either as separate formulations, wherein at least one of those formulations comprises compound of formula I, and at least one comprises the other therapeutic agent, or may be presented (i.e. formulated) as a combined preparation (i.e. presented as a single formulation including compound of formula I and the other therapeutic agent).

Thus, there is further provided:
(1) pharmaceutical formulations including a compound of formula I; another therapeutic agent useful in the treatment of cancer; and a pharmaceutically-acceptable adjuvant, diluent or carrier; and
(2) kits of parts comprising components:
   (a) a pharmaceutical formulation including a compound of formula I, in admixture with a pharmaceutically-acceptable adjuvant, diluent or carrier; and
   (b) a pharmaceutical formulation including another therapeutic agent useful in the treatment of cancer, in admixture with a pharmaceutically-acceptable adjuvant, diluent or carrier,
which components (a) and (b) are each provided in a form that is suitable for administration in conjunction with the other.

Components (a) and (b) of the kits of parts described herein may be administered simultaneously or sequentially.

According to a further embodiment of the invention, there is provided a method of making a kit of parts as defined above, which method comprises bringing component (a), as defined above, into association with a component (b), as defined above, thus rendering the two components suitable for administration in conjunction with each other.

By bringing the two components "into association with" each other, we include that components (a) and (b) of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(I) one of components (a) and (b) as defined herein; together with
(II) instructions to use that component in conjunction with the other of the two components.

The kits of parts described herein may comprise more than one formulation including an appropriate quantity/dose of compound of formula I, and/or more than one formulation including an appropriate quantity/dose of the other therapeutic agent, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising compound of formula I and the other therapeutic agent are administered, sequentially, separately and/or simultaneously, over the course of treatment of the relevant condition.

Thus, in respect of the combination product according to embodiments of the invention, the term "administration in conjunction with" includes that the two components of the combination product (compound of formula I and the other therapeutic agent) are administered (optionally repeatedly), either together, or sufficiently closely in time, to enable a beneficial effect for the patient, that is greater, over the course of the treatment of the relevant condition, than if either a formulation comprising compound of formula I, or a formulation comprising the other therapeutic agent, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to embodiments of the invention, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses of compound of formula I and the other therapeutic agent are administered within 48 hours (e.g. 24 hours) of each other.

The compounds/combinations/methods/uses described herein may have the advantage that, in the treatment of the conditions described herein, they may be more convenient for the physician and/or patient than, be more efficacious than, be less toxic than, have better selectivity, have a broader range of activity than, be more potent than, produce fewer side effects than, or may have other useful pharmacological properties over, similar compounds, combinations, methods (treatments) or uses known in the prior art for use in the treatment of those conditions or otherwise, for example over the compounds disclosed in international patent applications WO 2007/010273 and WO 2007/010281.

Further, such advantages may stem from the compounds of formula I being AMPK activators (e.g. especially where it is stated that the compounds described herein may have better selectivity, and may produce fewer side effects, e.g. gastrointestinal side effects).

Preferred, non-limiting examples which embody certain aspects of the invention will now be described, with reference to the following figures:

FIG. 1, which shows the effect of the compound of Example 1 or the compound of Example 2c on AMPK phosphorylation. After starvation of PC3 cells in serum-free medium for 24 h, 0.3, 0.6, 1.2 and 2.5 µM of the compound of Example 1 or the compound of Example 2c was added and incubated for an additional 4 h. The Figure provides representative immunoblots of AMPK phosphorylation by the compound of Example 1 or the compound of Example 2c. The compound of Example 1 and the compound of Example 2c stimulates AMPK phosphorylation in PC3 cells.

Figure 2:
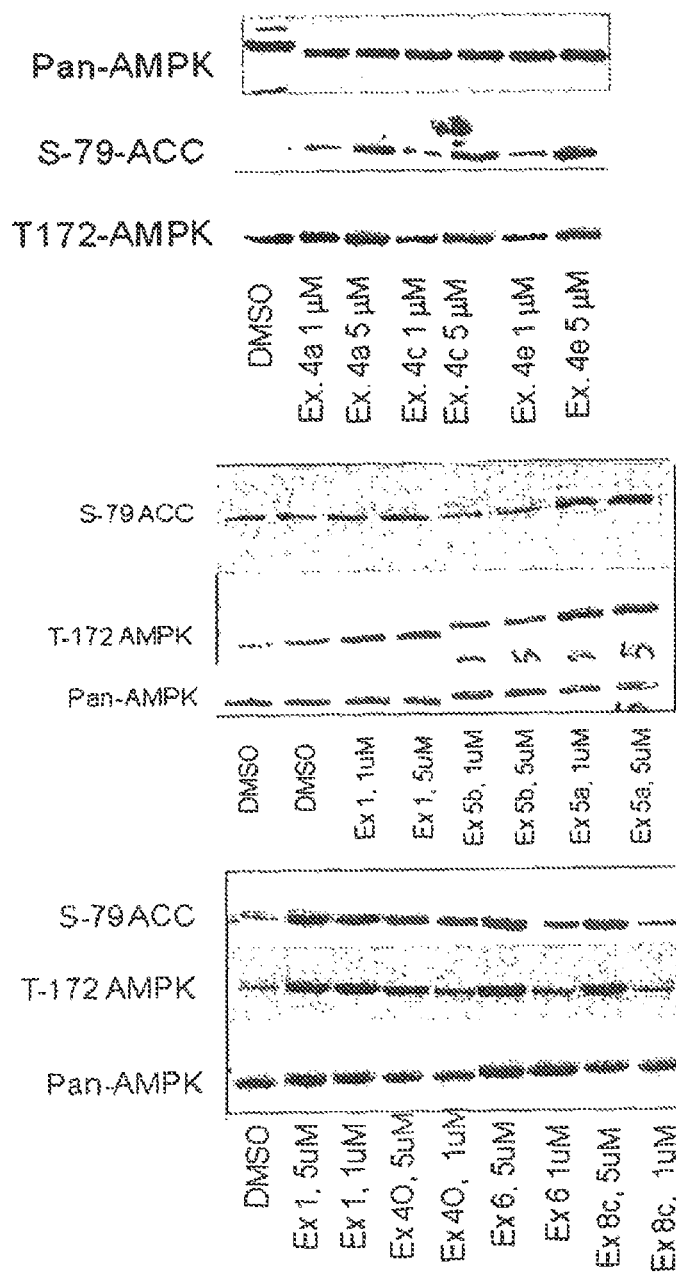

FIG. 2, which shows the effect of the compound of selected compounds of the examples on AMPK phosphorylation in comparison to total AMPK levels, and on acetyl co-enzyme A (acetyl-CoA) carboxylase phosphorylation (a substrate of AMPK). After starvation of PC3 cells in serum-free medium for 16 h, 1 and 5 µM of the selected compounds were added and incubated for an additional 4 h. The Figure provides representative immunoblots of the total level of AMPK (Pan-AMPK) and the level of AMPK and acetyl-CoA carboxylase phosphorylation by the selected compounds of the examples. The selected compounds of the examples stimulate AMPK phosphorylation in PC3 cells and induce the phosphorylation of acetyl-CoA carboxylase.

Figure 3:
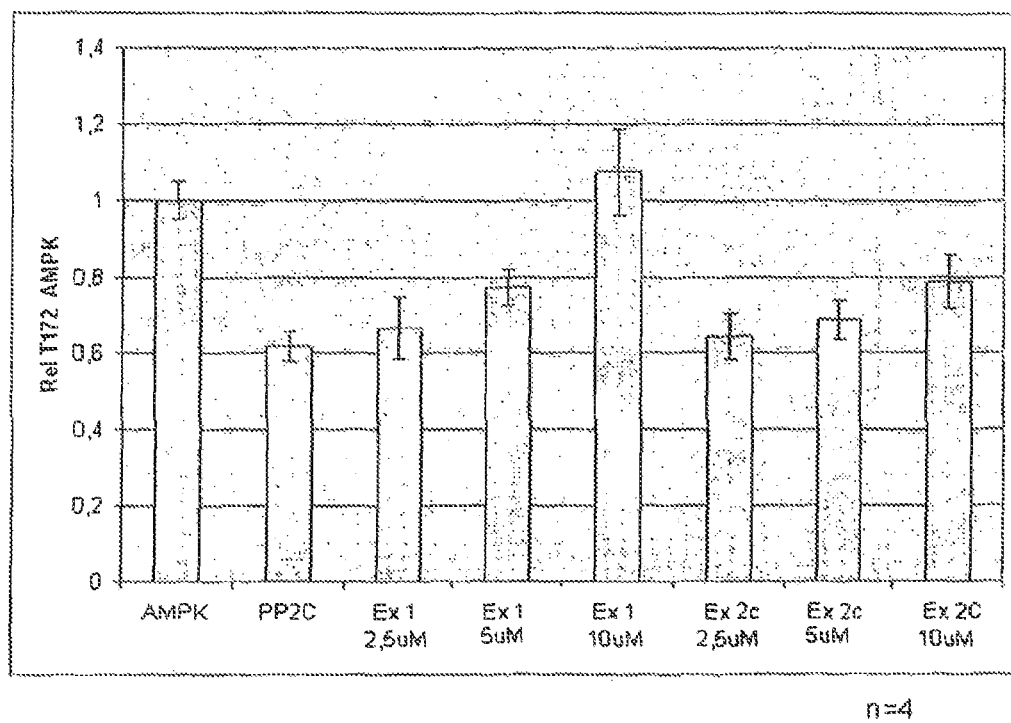

FIG. 3, which shows that the compound of Example 1 and 2c can reduce PP2C-α1 mediated dephosphorylation of AMPK. The compounds were tested in the assay at concentrations of 2.5, 5 and 10 µM (as depicted in the figure).

EXAMPLES

The invention is illustrated by the following examples, in which the following abbreviations may be employed:

BrdU 5-bromo-2-deoxyuridine
nBuLi N-butyl lithium
DCM dichloromethane
DMF dimethylformamide
DMSO dimethylsulfoxide
ES electro spray
Et₂O diethyl ether
EtOAc ethyl acetate
EtOH ethanol
LC liquid chromatography
MeOH methanol
MS mass spectrometry
MTBE methyl tert-butyl ether
NMR nuclear magnetic resonance
THF tetrahydrofuran Where no preparative routes are included, the relevant intermediate is commercially available (e.g. from Chemical Diversity, San Diego, Calif., USA or other available commercial sources).

General Procedures

LC-MS was performed on a Sciex API 150 LC/ES-MS equipped with an ACE 3 C8 column (30×3.0 mm) using a flow of 1 mL/min. Two gradient systems of acetonitrile in water (with 0.1% TFA) are used for elution: A) 5-100% under 10 min, then 2 min 100% isocratic or B) 90-100% under 2 min, then 2 min 100% isocratic. Direct inlet ES-MS was also performed on a Bruker Esquire LC/ES-MS. ¹H nuclear magnetic resonance was recorded on a Bruker Avance DRX 400 spectrometer at 400.01 MHz using residual solvent as internal standard.

General Procedure for Synthesis of Benzoyl Isothiocyanates from Benzoyl Chlorides To a mixture of the benzoyl chloride (5 mmol) and tributylamine bromide (0.15 mmol) in toluene (10 mL) was added Potassium isothiocyanate (13 mmol) in water (10 mL) at rt. The mixture was stirred at r.t for 18 h. The phases were separated and the aq. phase was extracted with toluene (2×20 mL). The combined organic phases were dried over MgSO4, filtered through a short plug of silica gel and evaporated to yield the benzoyl isothiocyanate with high purity according to 1H NMR. The material is used in the next step without further purification.

Example 1

5-(3,4-dichlorophenyl)imino-4-[[3-(trifluoromethyl)phenyl]methyl]-1,2,4-thiadiazolidin-3-one

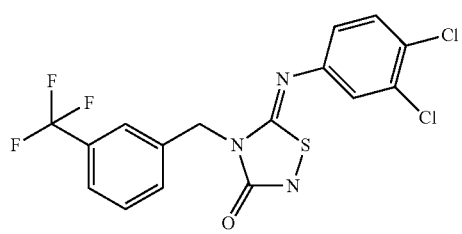 [SMILES: O=c1[nH]s/c(=N\c2ccc(Cl)c(Cl)c2)n1Cc1cccc(C(F)(F)F)c1]

(i) 1-[(3,4-dichlorophenyl)carbamothioyl]-1-[[3-(trifluoromethyl)phenyl]methyl]urea To a solution of 3-trifluoromethyl benzyl urea (218 mg, 1 mmol) in dry THF (2 mL) under nitrogen was added dropwise n-BuLi (2.5 M in hexane, 0.4 mL). The mixture was stirred at RT for 30 min and then 3,4-dichlorophenyl isothiocyanate (204 mg, 1 mmol) in dry THF (2 mL) was added dropwise. HPLC analysis after 5 min revealed complete reaction to the expected product. Saturated NaHCO₃ (5 mL) and Et₂O (15 mL) were added and the phases were separated. The aqueous phase was extracted with Et₂O (2×15 mL). The combined organic phases were washed with brine (5 mL) and were dried over MgSO₄. Concentration in vacuo gave 412 mg of a yellow oil. Purification by flash chromatography (silica, 20-30% EtOAc in n-hexane) gave 193 mg (46%) of pure product according to ¹H NMR.

MS: m/z: 422 (M+H); Purity (HPLC): 95.2%; ¹H NMR (500 MHz, Chloroform-d) δ ppm 13.34 (s, 1H) 7.81 (s, 1H) 7.54-7.65 (m, 4H) 7.47 (s, 2H) 5.82 (s, 2H) 5.02 (br. s., 2H)

(ii) 5-(3,4-dichlorophenyl)imino-4-[[3-(trifluoromethyl)phenyl]methyl]-1,2,4-thiadiazolidin-3-one Bromine (16 mg in 0.5 mL of EtOH) was added dropwise to a solution of 1-[(3,4-dichlorophenyl)carbamothioyl]-1-[[3-(trifluoromethyl)phenyl]methyl]urea (42 mg, 0.1 mmol) in 0.5 mL EtOH at 0° C. HPLC-MS analysis revealed almost complete conversion to product after 30 min of stirring. The reaction was worked up after 1.5 h. Water (3 mL) was added and the resulting aqueous phase was extracted with Et₂O (3×15 mL). The combined organic phases were washed with brine, dried over Na₂SO₄ and concentrated in vacuo to yield 43.5 mg of crude material (approximately 90% purity). The material was purified by preparative HPLC (basic conditions) XTerra Prep MS C18 5 mm 19×50 mm column, flow 25 ml/min, 50 mM pH10 NH4HCO3/ACN, 5-97% ACN in 6 min, fractions collected based on UV-signal (254 nm) to give the product in 21.7 mg (52%). HPLC purity: 98.5%, MS: m/z: 420 (M+H), 1H NMR (500 MHz, Chloroform-d) δ ppm 7.81 (s, 1H) 7.70 (d, J=7.81 Hz, 1H) 7.60 (d, J=7.81 Hz, 1H) 7.49 (t, J=7.69 Hz, 1H) 7.40 (d, J=8.55 Hz, 1H) 7.06 (d, J=2.44 Hz, 1H) 6.79 (dd, J=8.55, 2.44 Hz, 1H) 5.04 (s, 2H).

Example 2

The following compounds were (compounds (c) and (e)), or may be prepared using procedures described in the specification above.

a) 5-(3,4-dichlorophenyl)imino-4-[(4-methoxyphenyl)methyl]-1,2,4-thiadiazolidin-3-one

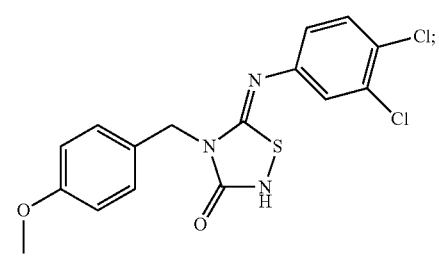 [SMILES: COc1ccc(Cn2c(=O)[nH]s/c2=N\c2ccc(Cl)c(Cl)c2)cc1]

b) 4-[(4-chlorophenyl)methyl]-5-(3,4-dichlorophenyl)imino-1,2,4-thiadiazolidin-3-one

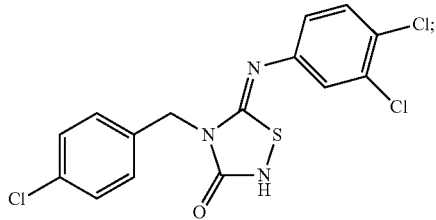 [SMILES: O=c1[nH]s/c(=N\c2ccc(Cl)c(Cl)c2)n1Cc1ccc(Cl)cc1]

c) 5-(3,4-dichlorophenyl)imino-4-[(3,4-difluorophenyl)methyl]-1,2,4-thiadiazolidin-3-one

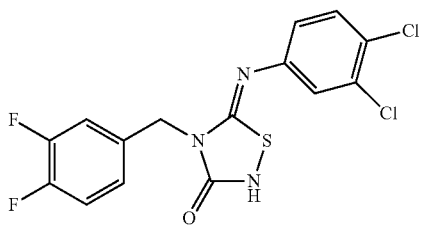 [SMILES: O=c1[nH]s/c(=N\c2ccc(Cl)c(Cl)c2)n1Cc1ccc(F)c(F)c1]

$^1$H NMR (500 MHz, Methanol-d$_4$) δ ppm 7.48 (d, J=8.55 Hz, 1H) 7.39 (ddd, J=11.35, 7.81, 1.83 Hz, 1H) 7.22-7.31 (m, 2H) 7.15 (d, J=2.44 Hz, 1H) 6.92 (dd, J=8.55, 2.69 Hz, 1H) 4.97 (s, 2H). ESI MS m/z=388 [M+H]$^+$;

d) 5-(3,4-dichlorophenyl)imino-4-[(3-fluorophenyl)methyl]-1,2,4-thiadiazolidin-3-one

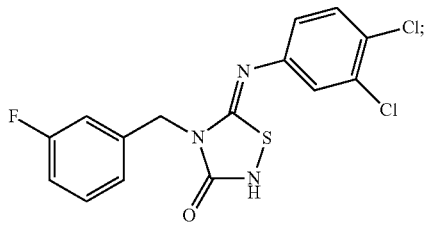 [SMILES: O=c1[nH]s/c(=N\c2ccc(Cl)c(Cl)c2)n1Cc1cccc(F)c1]

e) 5-(3,4-dichlorophenyl)imino-4-[phenyl)methyl]-1,2,4-thiadiazolidin-3-one

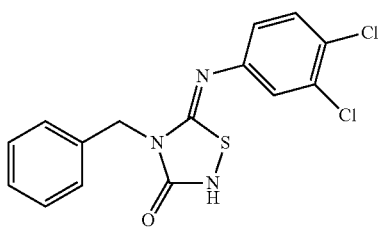 [SMILES: O=c1[nH]s/c(=N\c2ccc(Cl)c(Cl)c2)n1Cc1ccccc1]

$^1$H NMR (500 MHz, Methanol-d$_4$) δ ppm 7.47 (d, J=8.55 Hz, 1H) 7.45 (d, J=7.32 Hz, 2H) 7.35 (t, J=7.32 Hz, 2H) 7.28-7.33 (m, 1H) 7.14 (d, J=2.44 Hz, 1H) 6.92 (dd, J=8.55, 2.44 Hz, 1H) 5.01 (s, 2H). ESI MS m/z=352 [M+H]$^+$;

f) 5-(3,4-dichlorophenyl)imino-4-phenethyl-1,2,4-thiadiazolidin-3-one

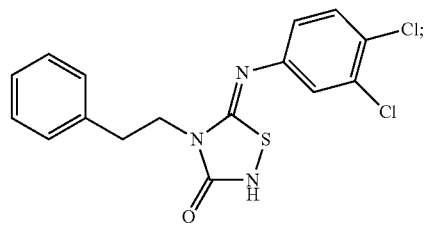 [SMILES: O=c1[nH]s/c(=N\c2ccc(Cl)c(Cl)c2)n1CCc1ccccc1]

g) 4-[2-[(4-chlorophenyl)-methyl-amino]ethyl]-5-(3,4-dichlorophenyl)imino-1,2,4-thiadiazolidin-3-one

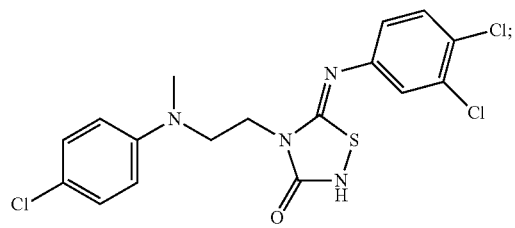 [SMILES: CN(CCn1c(=O)[nH]s/c1=N\c1ccc(Cl)c(Cl)c1)c1ccc(Cl)cc1]

h) 4-[2-(4-chlorophenyl)sulfanylethyl]-5-(3,4-dichlorophenyl)imino-1,2,4-thiadiazolidin-3-one

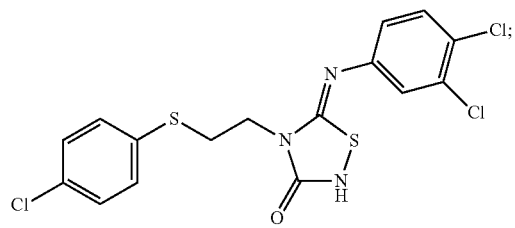 [SMILES: O=c1[nH]s/c(=N\c2ccc(Cl)c(Cl)c2)n1CCSc1ccc(Cl)cc1]

i) 3-[[(5-(3,4-dichlorophenyl)imino-3-oxo-1,2,4-thiadiazolidin-4-yl]methyl]-N-methylbenzamide

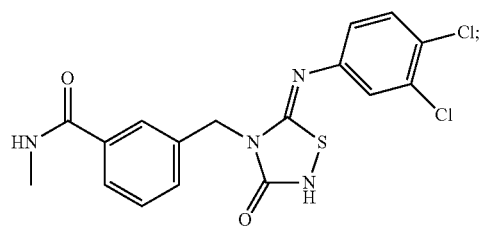 [SMILES: CNC(=O)c1cccc(Cn2c(=O)[nH]s/c2=N\c2ccc(Cl)c(Cl)c2)c1]

j) 5-[(6-chloro-3-pyridyl)imino]-4-[(3,4-difluorophenyl)methyl]-1,2,4-thiadiazolidin-3-one

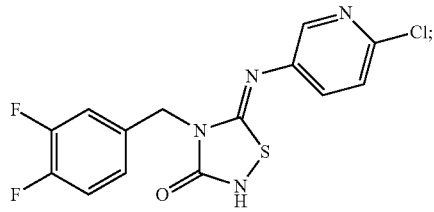 [SMILES: O=c1[nH]s/c(=N\c2ccc(Cl)nc2)n1Cc1ccc(F)c(F)c1]

k) 4-[[4-[(3,4-difluorophenyl)methyl]-3-oxo-1,2,4-thiadiazolidin-5-ylidene]amino]benzonitrile

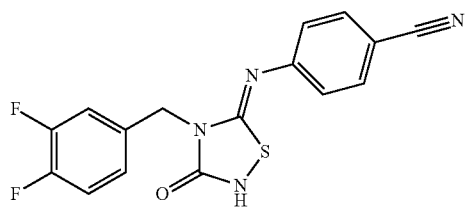 [SMILES: N#Cc1ccc(/N=c2\s[nH]c(=O)n2Cc2ccc(F)c(F)c2)cc1]

l) 4-[(3,4-difluorophenyl)methyl]-5-[4-(trifluoromethyl)phenyl]imino-1,2,4-thiadiazolidin-3-one

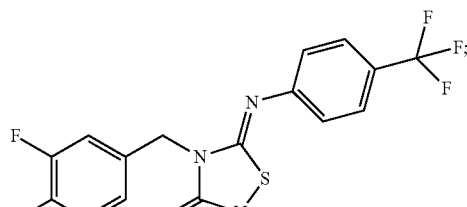

m) 4-[(3,4-difluorophenyl)methyl]-5-[4-(trifluoromethoxy)phenyl]imino-1,2,4-thiadiazolidin-3-one

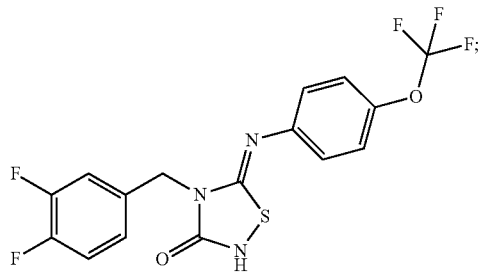 [SMILES: O=c1[nH]s/c(=N\c2ccc(OC(F)(F)F)cc2)n1Cc1ccc(F)c(F)c1]

n) 3-[5-(3,4-dichlorophenyl)imino-3-oxo-1,2,4-thiadiazolidin-4-yl]methyl]benzonitrile

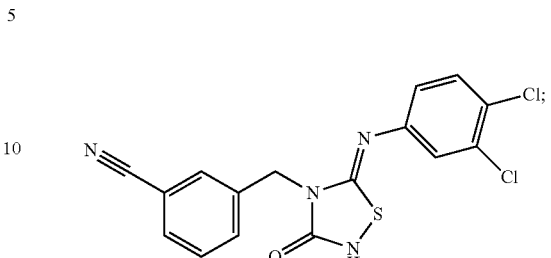

o) 5-(3,4-dichlorophenyl)imino-4-[[4-(1,2,4-triazol-1-yl)phenyl]methyl]-1,2,4-thiadiazolidin-3-one

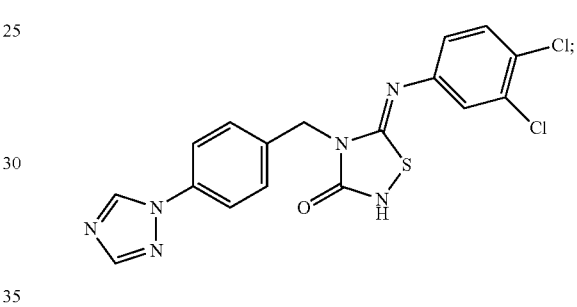

p) 4-[1-(4-chlorophenyl)cyclopropyl]-5-(4-chlorophenyl)imino-1,2,4-thiadiazolidin-3-one

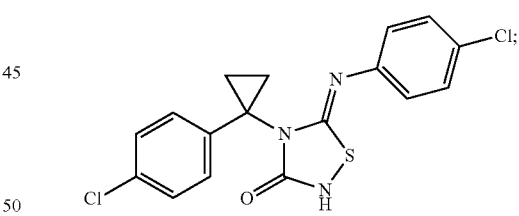

and q) 5-[(4-chlorophenyl)methylimino]-4-[(3,4-difluorophenyl)methyl]-1,2,4-thiadiazolidin-3-one

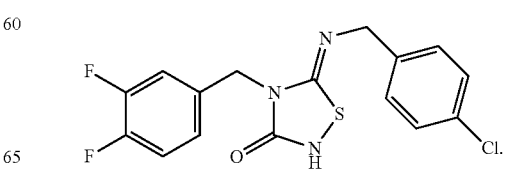

Example 3

N-[3-oxo-2-[[3-(trifluoromethyl)phenyl]methyl]-1,2,4-thiadiazol-5-yl]benzamide

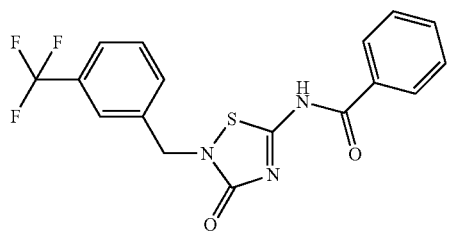 [SMILES: O=C(Nc1nc(=O)n(Cc2cccc(C(F)(F)F)c2)s1)c1ccccc1]

(i) N-[3-(3-Trifluoromethylbenzyl)-ureidocarbothioyl]-benzamide (3-Trifluoromethyl-benzyl)-urea (218 mg; 1.0 mmol) and 163 mg (1.0 mmol) benzoylisothiocyanate were dissolved in acetone and the mixture was heated to reflux. After 18 h of reflux HPLC-MS revealed almost complete conversion to expected product in a very clean reaction. The solvent was evaporated and the residue was dissolved in EtOAc (40 mL). Wash with 2M HCl (5 mL), water (2×5 mL) and brine (5 mL), and the organic phase was dried over MgSO4 and concentrated in vacuo to give 347 mg of a light yellow solid. HPLC-MS indicates a purity of approximately 90%.

Part of the crude material was used in the next step without further purification.

1H NMR (500 MHz, Methanol-$d_4$) δ ppm 7.95 (dd, J=8.30, 1.22 Hz, 2H) 7.68 (d, J=0.98 Hz, 1H) 7.65 (dd, J=8.79, 7.57 Hz, 2H) 7.59 (d, J=7.08 Hz, 1H) 7.51-7.57 (m, 3H) 4.63 (s, 2H).

(ii) N-[3-oxo-2-[[3-(trifluoromethyl)phenyl]methyl]-1,2,4-thiadiazol-5-yl]benzamide Bromine (17 mg in 0.5 mL of EtOH, 0.1 mmol) was added dropwise to a solution of 40 mg (0.1 mmol) N-[3-(3-trifluoromethylbenzyl)-ureidocarbothioyl]-benzamide (from step (i) above) in 3.5 mL EtOH at rt. HPLC-MS indicated complete reaction after 15 min. The solvent was removed in vacuo to give 51 mg of an orange solid. The solid was triturated with EtOAc to yield 25 mg (63%) of pure product as an off-white solid after drying.

30 MS: [M+H]: 380.0, HPLC purity: 99%.

1H NMR (500 MHz, Methanol-$d_4$) δ ppm 8.11 (dd, J=8.42, 1.10 Hz, 2H) 7.70 (s, 1H) 7.63-7.69 (m, 3H) 7.57-7.62 (m, 1H) 7.55 (t, J=7.69 Hz, 2H) 4.97 (s, 2H).

Example 4

The following compounds were (compounds (a) to (f) and (j) to (r)) or may be prepared using procedures described in the specification above.

a) 4-fluoro-N-[3-oxo-2-[[3-(trifluoromethyl)phenyl]methyl]-1,2,4-thiadiazol-5-yl]benzamide

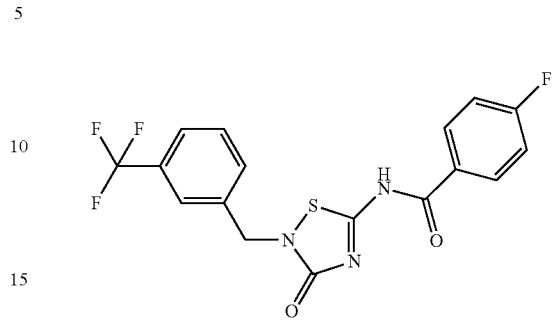

MS: [M+H]: 398.0, HPLC purity: 100%, 1H NMR (500 MHz, Methanol-$d_4$) δ ppm: 8.19 (dd, J=8.79, 5.37 Hz, 2H) 7.69 (s, 1H) 7.62-7.67 (m, 2H) 7.56-7.62 (m, 1H) 7.26 (t, J=8.79 Hz, 2H) 4.94 (s, 2H);

b) 2-(4-fluorophenyl)-N-[3-oxo-2-[[3-(trifluoromethyl)phenyl]methyl]-1,2,4-thiadiazol-5-yl]acetamide

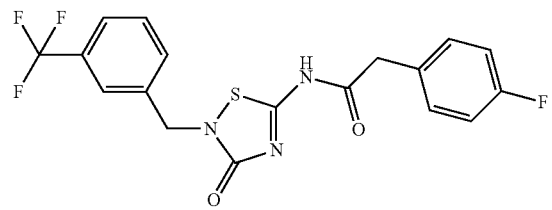 [SMILES: O=C(Cc1ccc(F)cc1)Nc1nc(=O)n(Cc2cccc(C(F)(F)F)c2)s1]

MS: [M+H]: 412, HPLC purity: 100%, 1H NMR (500 MHz, Methanol-$d_4$) δ ppm 7.64 (s, 1H) 7.60-7.63 (m, 1H) 7.57-7.60 (m, 1H) 7.53-7.57 (m, 1H) 7.31 (dd, J=8.55, 5.37 Hz, 2H) 7.06 (t, J=8.79 Hz, 2H) 4.95 (s, 2H) 3.86 (s, 2H);

c) 4-chloro-N-[2-[(3,4-difluorophenyl)methyl]-3-oxo-1,2,4-thiadiazol-5-yl]benzamide

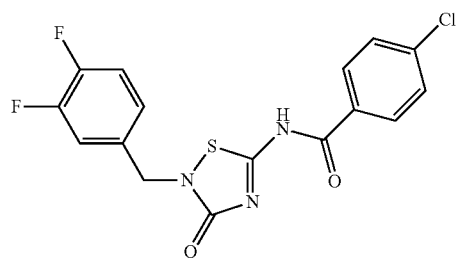 [SMILES: O=C(Nc1nc(=O)n(Cc2ccc(F)c(F)c2)s1)c1ccc(Cl)cc1]

MS: [M+H]: 382.0, HPLC purity: 100%, 1H NMR (500 MHz, DMSO-$d_6$) δ ppm 8.10 (d, J=8.79 Hz, 2H) 7.62 (d, J=8.30 Hz, 2H) 7.38-7.49 (m, 2H) 7.21 (ddd, J=6.23, 4.15, 2.08 Hz, 1H) 4.78 (s, 2H)

d) 4-chloro-N-[2-[(4-fluorophenyl)methyl]-3-oxo-1,2,4-thiadiazol-5-yl]benzamide

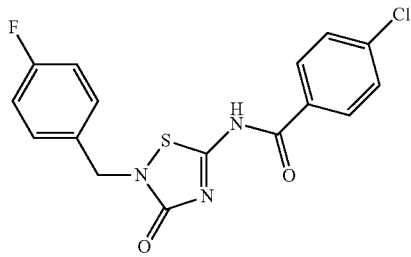 [SMILES: O=C(Nc1nc(=O)n(Cc2ccc(F)cc2)s1)c1ccc(Cl)cc1]

MS: [M+H]: 364.0, HPLC purity: 100%, 1H NMR (500 MHz, DMSO-d$_6$) δ ppm 8.10 (d, J=8.55 Hz, 2H) 7.62 (d, J=8.79 Hz, 2H) 7.41 (dd, J=8.67, 5.49 Hz, 2H) 7.21 (t, J=8.91 Hz, 2H) 4.78 (s, 2H);

e) 4-chloro-N-[2-[(4-chlorophenyl)methyl]-3-oxo-1,2,4-thiadiazol-5-yl]benzamide

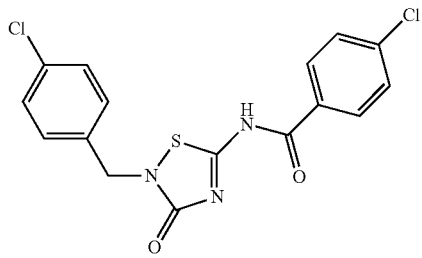 [SMILES: O=C(Nc1nc(=O)n(Cc2ccc(Cl)cc2)s1)c1ccc(Cl)cc1]

MS: [M+H]: 380.0, HPLC purity: 100%, 1H NMR (500 MHz, DMSO-d$^6$) δ ppm 8.10 (d, J=8.55 Hz, 2H) 7.63 (d, J=8.55 Hz, 2H) 7.44 (d, J=8.55 Hz, 2H) 7.38 (d, J=8.55 Hz, 2H) 4.79 (s, 2H);

f) 4-chloro-N-[2-[2-(phenoxy)ethyl]-3-oxo-1,2,4-thiadiazol-5-yl]benzamide

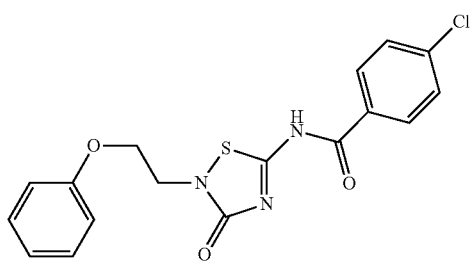 [SMILES: O=C(Nc1nc(=O)n(CCOc2ccccc2)s1)c1ccc(Cl)cc1]

MS: [M+H]: 377.0, HPLC purity: 100%, 1H NMR (500 MHz, DMSO-d6) δ ppm 8.12 (d, J=8.55 Hz, 2H) 7.63 (d, J=8.79 Hz, 2H) 7.30 (dd, J=8.55, 7.32 Hz, 2H) 6.93-6.99 (m, 3H) 4.20 (t, J=5.00 Hz, 2H) 3.97 (t, J=5.01 Hz, 2H);

g) 4-chloro-N-[2-[2-[(4-chlorophenyl)-methylamino]ethyl]-3-oxo-1,2,4-thiadiazol-5-yl]benzamide

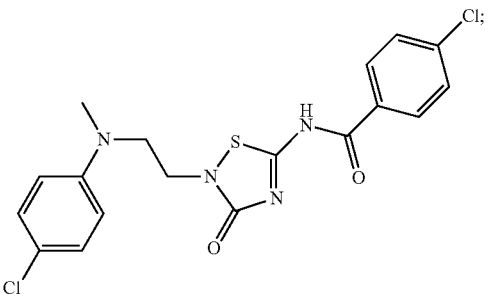 [SMILES: CN(CCn1sc(NC(=O)c2ccc(Cl)cc2)nc1=O)c1ccc(Cl)cc1]

h) 4-chloro-N-[2-[2-(4-chlorophenyl)sulfanylethyl]-3-oxo-1,2,4-thiadiazol-5-yl]benzamide

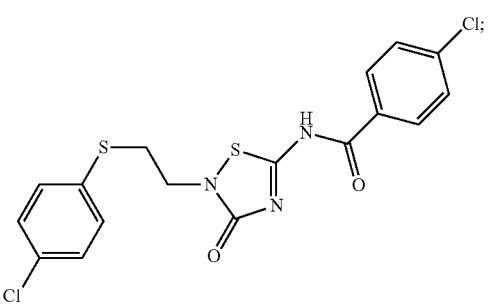 [SMILES: O=C(Nc1nc(=O)n(CCSc2ccc(Cl)cc2)s1)c1ccc(Cl)cc1]

i) 3,4-dichloro-N-[2-[1-(4-fluorophenyl)cyclopropyl]-3-oxo-1,2,4-thiadiazol-5-yl]benzamide

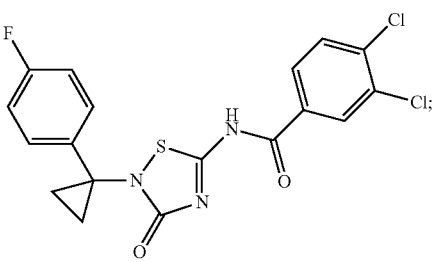 [SMILES: O=C(Nc1nc(=O)n(C2(c3ccc(F)cc3)CC2)s1)c1ccc(Cl)c(Cl)c1]

j) 3,4-dichloro-N-[2-[(4-fluorophenyl)methyl]-3-oxo-1,2,4-thiadiazol-5-yl]benzamide

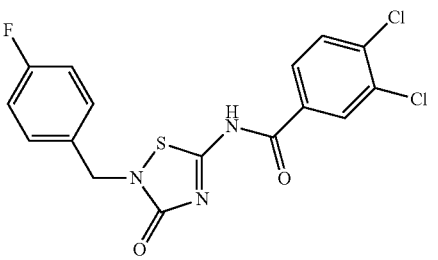 [SMILES: O=C(Nc1nc(=O)n(Cc2ccc(F)cc2)s1)c1ccc(Cl)c(Cl)c1]

1H NMR (500 MHz, DMSO-d$_6$) δ ppm 4.78 (s, 2H) 7.18-7.24 (m, 2H) 7.38-7.43 (m, 2H) 7.83 (d, J=8.30 Hz, 1H) 8.02 (dd, J=8.55, 1.95 Hz, 1H) 8.24 (d, J=1.95 Hz, 1H);

k) N-[2-[(4-fluorophenyl)methyl]-3-oxo-1,2,4-thiadiazol-5-yl]-4-methoxy-benzamide

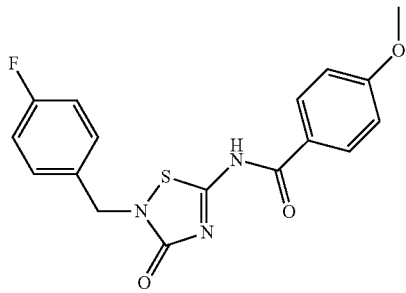 [SMILES: COc1ccc(C(=O)Nc2nc(=O)n(Cc3ccc(F)cc3)s2)cc1]

MS: [M+H]: 360, HPLC purity: 95%;

l) 2,6-dichloro-N-[2-[(4-fluorophenyl)methyl]-3-oxo-1,2,4-thiadiazol-5-yl]benzamide

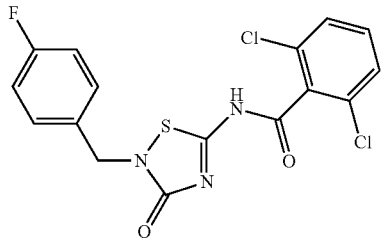 [SMILES: O=C(Nc1nc(=O)n(Cc2ccc(F)cc2)s1)c1c(Cl)cccc1Cl]

MS: [M+H]: 398, HPLC purity: 95%;

m) 2,4-dichloro-N-[2-[(4-fluorophenyl)methyl]-3-oxo-1,2,4-thiadiazol-5-yl]benzamide

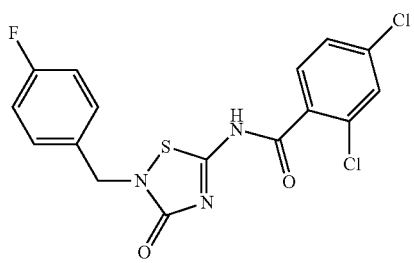 [SMILES: O=C(Nc1nc(=O)n(Cc2ccc(F)cc2)s1)c1ccc(Cl)cc1Cl]

MS: [M+H]: 398, HPLC purity: 98%
1H NMR (500 MHz, DMSO-$d_6$) δ ppm 4.80 (s, 2H) 7.19-7.24 (m, 2H) 7.39-7.44 (m, 2H) 7.60 (dd, J=8.42, 2.08 Hz, 1H) 7.79 (d, J=1.71 Hz, 1H) 7.91 (br. s., 1H) 13.71 (br. s., 1H);

n) N-[2-[(4-fluorophenyl)methyl]-3-oxo-1,2,4-thiadiazol-5-yl]-4-(trifluoromethoxy)-benzamide

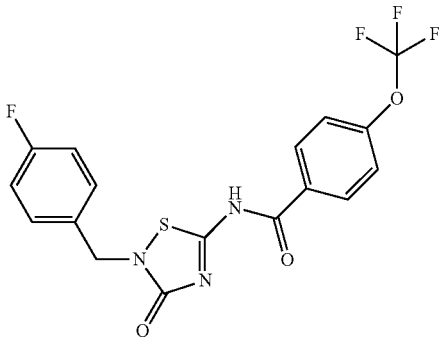 [SMILES: O=C(Nc1nc(=O)n(Cc2ccc(F)cc2)s1)c1ccc(OC(F)(F)F)cc1]

MS: [M+H]: 414, HPLC purity: 100%;

o) N-[2-[(4-fluorophenyl)methyl]-3-oxo-1,2,4-thiadiazol-5-yl]-3,5-bis(trifluoromethyl)-benzamide

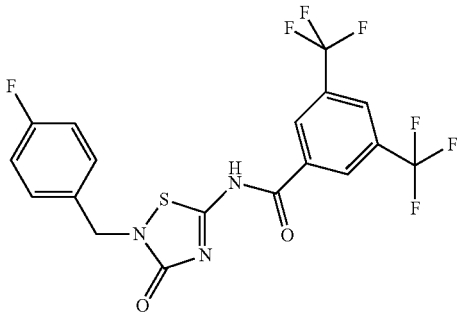 [SMILES: O=C(Nc1nc(=O)n(Cc2ccc(F)cc2)s1)c1cc(C(F)(F)F)cc(C(F)(F)F)c1]

MS: [M+H]: 466, HPLC purity: 95%;

p) 3,4-difluoro-N-[2-[(4-fluorophenyl)methyl]-3-oxo-1,2,4-thiadiazol-5-yl]benzamide

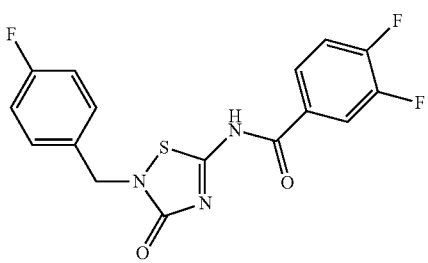 [SMILES: O=C(Nc1nc(=O)n(Cc2ccc(F)cc2)s1)c1ccc(F)c(F)c1]

MS: [M+H]: 366, HPLC purity: 100%;

q) 2-chloro-6-fluoro-N-[2-[(4-fluorophenyl)methyl]-3-oxo-1,2,4-thiadiazol-5-yl]benzamide

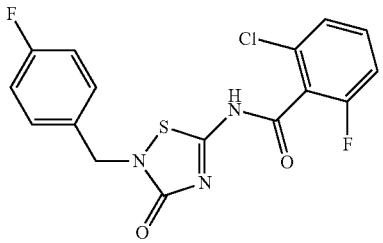 [SMILES: O=C(Nc1nc(=O)n(Cc2ccc(F)cc2)s1)c1c(F)cccc1Cl]

MS: [M+H]: 382, HPLC purity: 100%; and r) 3,5-difluoro-N-[2-[(4-fluorophenyl)methyl]-3-oxo-1,2,4-thiadiazol-5-yl]benzamide

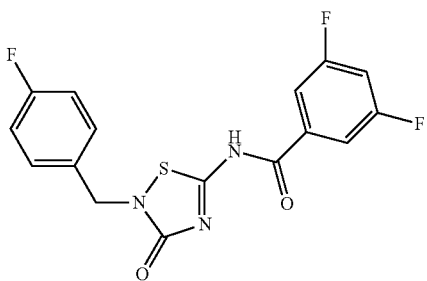 [SMILES: O=C(Nc1nc(=O)n(Cc2ccc(F)cc2)s1)c1cc(F)cc(F)c1]

MS: [M+H]: 366, HPLC purity: 95%.

Compounds 4j-4r were synthesized from a compound of formula III by reaction with compounds of formula IV wherein $L_2$ is chlorine and $W^1$ is —C(O)— (Substituted benzoylchloride).

Compounds 4j-4r were synthesized as a small compound library in the following way: 5-Amino-2-(4-fluoro-benzyl)-[1,2,4]thiadiazol-3-one and pyridine were mixed in 400 µl of acetonitrile. The acid chloride in 100 µl of acetonitrile was added. The reactions were stirred overnight. 50 µl 2 M KOH was added to hydrolyse the disubstituted biproduct. After 1 day was the reactions acidified with 100 µl of TFA, diluted to 2 ml with DMSO/methanol/water and purified with reversed phase chromatography (ACE C8, 5 µm, 21×50 mm, flow 25 ml/min, gradient: water+0.1% TFA/acetonitrile over 6 minutes).

Example 5 a) 5-(3,4-dichlorophenyl)imino-4-(2-phenoxyethyl)-1,2,4-thiadiazolidin-3-one; and b) 5-(3,4-Dichloro-phenylamino)-2-(2-phenoxy-ethyl)-[1,2,4]thiadiazol-3-one

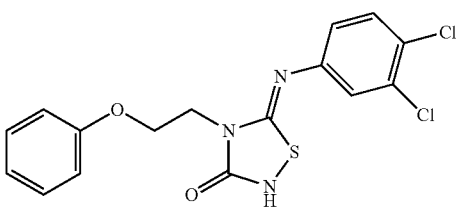

5a

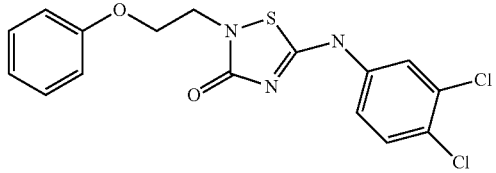

5b

(i)(2-Phenoxy-ethyl)-urea

2-Phenoxyethyl amine (137 mg, 1 mmol) and urea (300 mg, 5 mmol) were placed in a 2 mL microwave vial. Conc. HCl (200 µL) and water (500 µL) were added and the mixture was heated to 150° C. for 30 min under microwave irradiation. After cooling the vial was full of white precipitate. The solid was collected by filtration, and was washed with several portions of water. After drying in a vacuum dessicator 167 mg (93%) of product as a white crystalline material was isolated. HPLC-MS revealed that the product consisted of a mixture of 67% product and 33% dialkylated product. Purification by flash chromatography: (silica, 4-5% MeOH in CH2Cl2) gave 79 mg (44%) of pure product as a white solid.

1H NMR (500 MHz, Methanol-$d_4$) δ ppm 7.28 (dd, J=8.91, 7.20 Hz, 2H) 6.90-6.99 (m, 3H) 4.02 (t, J=5.37 Hz, 2H) 3.51 (t, J=5.37 Hz, 2H)

(ii) (a) 1-[(3,4-dichlorophenyl)carbamothioyl]-1-(2-phenoxyethyl)urea

(b) 1-[(3,4-dichlorophenyl)carbamothioyl]-1-(2-phenoxyethyl)urea

To a solution of (2-phenoxyethyl)-urea (79 mg, 0.44 mmol, from step (i) above) in dry THF (2 mL) was added dropwise n-BuLi. The mixture was stirred at room temperature for 15 min and then the 3,4-dichlorophenylisothiocyanate (89 mg, 044 mmol) in dry THF (2 mL) was added dropwise HPLC after 1.5 h revealed almost complete disappearance of the starting material. Sat. NaHCO$_3$ (5 mL) and EtOAc (20 mL) were added and the phases were separated. The aq phase was extracted with another 20 mL of EtOAc. The combined org phases were washed with water (5 mL), brine (5 mL) and were dried over MgSO$_4$. Conc in vacuo gave 158 mg of a yellow oil HPLC-MS revealed two products with with the expected molecular weight, m/z=384

Purification by flash chromatography (silica, 30% EtOAc in n-hexane) gave to products a: 29 mg Tr=2.875 min (ACE, 10-97% CH3CN in 3 min, 1 mL/min): 73% purity, m/z=384 b: 34 mg (Fr 11-16) Tr=2.908 min (ACE, 10-97% CH3CN in 3 min, 1 mL/min): 97% purity, m/z=384

The two products were not further characterized. They were cyclized in two separate experiments.

iii) (a) 5-(3,4-dichlorophenyl)imino-4-(2-phenoxy-ethyl)-1,2,4-thiadiazolidin-3-one

(b) 5-(3,4-dichlorophenylamino)-2-(2-phenoxy-ethyl)-[1,2,4]thiadiazol-3-one Cyclisation of the compounds of step (ii)(a) and (ii)(b) to the products was performed according to the process set out in Example 1 step (ii). Purification with RP-HPLC gave the desired compounds.

5(a): MS: [M+H]: 385.0, HPLC purity: 97%, 1H NMR (500 MHz, DMSO-d6) δ ppm 7.42 (d, J=8.67 Hz, 1H) 7.24-7.31 (m, 2H) 7.05 (d, J=2.44 Hz, 1H) 6.99-7.03 (m, 2H) 6.92 (tt, J=7.32, 1.04 Hz, 1H) 6.87 (dd, J=8.67, 2.52 Hz, 1H) 4.10-4.16 (m, 2H) 3.95-4.02 (m, 2H)

5(b)b: MS: [M+H]385.0, HPLC purity: 100%; 1H NMR (500 MHz, DMSO-d6) δ ppm 11.01 (s, 1H) 8.05 (d, J=2.20 Hz, 1H) 7.62 (d, J=8.79 Hz, 1H) 7.44 (dd, J=8.79, 2.44 Hz, 1H) 7.27-7.34 (m, 2H) 6.93-6.99 (m, 3H) 4.17 (t, J=4.88 Hz, 2H) 4.00 (t, J=4.88 Hz, 2H).

Example 6

4-Benzhydryl-5-(3,4-dichlorophenyl)imino-1,2,4-thiadiazolidin-3-one

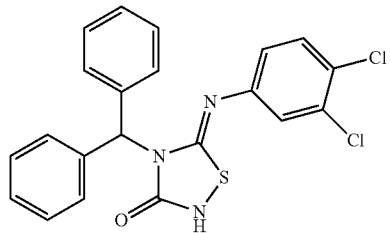 [SMILES: O=c1[nH]s/c(=N\c2ccc(Cl)c(Cl)c2)n1C(c1ccccc1)c1ccccc1]

The following compound was formed using the same methods as described for Examples 1 and 5 with the appropriate starting materials, except for the last cyclisation step where EtOAc was used instead of EtOH as solvent.

MS: m/z=428 [M+H]$^+$, HPLC purity: 98% (ACE), 96% (XTerra); 1H NMR (500 MHz, DMSO-d$_6$) δ ppm 10.95 (br. s., 1H) 8.02 (br. s., 1H) 7.61 (d, J=8.79 Hz, 1H) 7.38-7.45 (m, 5H) 7.33-7.38 (m, 2H) 7.22 (d, J=7.32 Hz, 4H) 6.62 (s, 1H).

Example 7 a) 4-chloro-N-[4-[(4-fluorophenyl)methyl]-3-oxo-1,2,4-thiadiazolidin-5-ylidene]benzamide

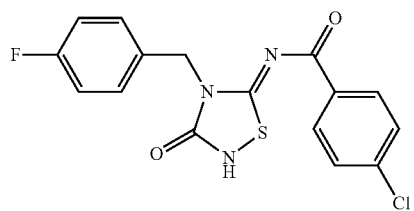 [SMILES: O=C(/N=c1\s[nH]c(=O)n1Cc1ccc(F)cc1)c1ccc(Cl)cc1]

(i) N-(carbamoylcarbamothioyl)-4-chloro-benzamide

4-Chlorobenzoyl isothiocyanate (395 mg) and 600 mg urea (5 equiv) were mixed in 30 mL of acetone and stirred at reflux for 1 day. The reaction was concentrated and the residue slurried in diethyl ether. The residue was collected by filtration and washed with diethyl ether. The white solid was dissolved in ethyl acetate (10 ml) and the resultant solution washed with water (10 ml) and brine (10 ml), dried over MgSO$_4$, filtered and concentrated to a white solid (0.35 g, 1.4 mmol, 70% yield.

(ii) 4-chloro-N-(3-oxo-1,2,4-thiadiazol-5-yl)benzamide

N-(Carbamoylcarbamothioylyl)-4-chloro-benzamide (350 mg) from step (i) above was mixed with 50 mL of ethyl acetate. Bromine (224 mg) in 5 mL of ethyl acetate was added. After 30 minutes 10 mL of water and 10 mL of methanol was added. The mixture was concentrated and the residue was triturated with water/methanol and dried in vacuum to give the product as a white solid, 0.25 g, 0.98 mmol, 70% yield.

(iii) 3,4-dichloro-N-[4-[(4-fluorophenyl)methyl]-3-oxo-1,2,4-thiadiazolidin-5-ylidene]benzamide 4-Chloro-N-(3-oxo-1,2,4-thiadiazol-5-yl)benzamide (50 mg, 0.20 mmol, 1 eq) and 55 mg (0.40 mmol, 2 eq) of potassium carbonate were mixed in 5 mL of DMF. 4-Fluorobenzyl bromide 38 mg (0.20 mmol, 1 eq) in 2 mL of DMF was added dropwise. The mixture was stirred for 15 min and then the reaction mixture was diluted with 100 mL of ethyl acetate and 100 mL of water. The organic phase was washed with 2×100 mL of water and 50 mL of brine, dried over MgSO$_4$, filtered and concentrated. The residue was purified with flash chromatography (silica, 40% EtOAc in hexane) to give the product as a white solid, 8 mg, 22 umol, 11%.

1H NMR (500 MHz, DMSO-d$_6$) δ ppm 5.17 (s, 2H) 7.16-7.22 (m, 2H) 7.50-7.56 (m, 2H) 7.61-7.65 (m, 2H) 8.19-8.23 (m, 2H) 10.46 (br. s., 1H), MS: [M+H], HPLC purity: 93%

The following compounds may be prepared according to the methods disclosed in for Example 7(a):

b) 4-chloro-N-[4-[(4-chlorophenyl)methyl]-3-oxo-1,2,4-thiadiazolidin-5-ylidene]benzamide

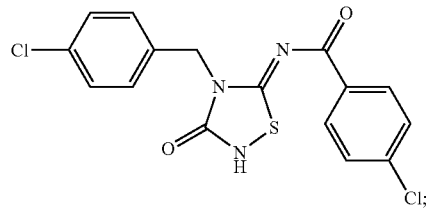 [SMILES: O=C(/N=c1\s[nH]c(=O)n1Cc1ccc(Cl)cc1)c1ccc(Cl)cc1]

c) 4-chloro-N-[3-oxo-4-[[3-(trifluoromethyl)phenyl]methyl]-1,2,4-thiadiazolidin-5-ylidene]benzamide

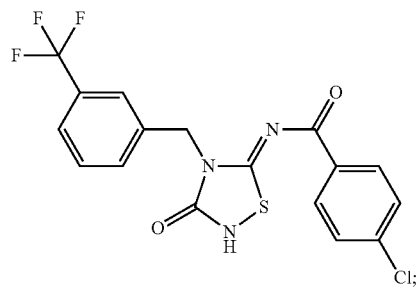 [SMILES: O=C(/N=c1\s[nH]c(=O)n1Cc1cccc(C(F)(F)F)c1)c1ccc(Cl)cc1]

d) N-[4-[(3-fluorophenyl)methyl]-3-oxo-1,2,4-thiadiazolidin-5-ylidene]-4-(trifluoromethyl)benzamide

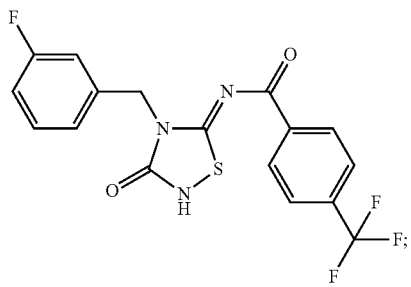 [SMILES: O=C(/N=c1\s[nH]c(=O)n1Cc1cccc(F)c1)c1ccc(C(F)(F)F)cc1]

e) N-[4-[(3-fluorophenyl)methyl]-3-oxo-1,2,4-thiadiazolidin-5-ylidene]-3,5-bis(trifluoromethyl)benzamide

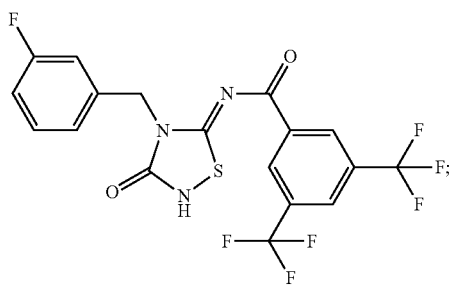 [SMILES: O=C(/N=c1\s[nH]c(=O)n1Cc1cccc(F)c1)c1cc(C(F)(F)F)cc(C(F)(F)F)c1]

f) N-[4-[(3,4-dichlorophenyl)methyl]-3-oxo-1,2,4-thiadiazolidin-5-ylidene]-3,4-difluorobenzamide

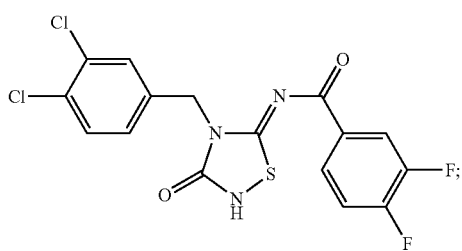 [SMILES: O=C(/N=c1\s[nH]c(=O)n1Cc1ccc(Cl)c(Cl)c1)c1ccc(F)c(F)c1]

and g) 3,4-dichloro-N-[4-[(4-fluorophenyl)methyl]-3-oxo-1,2,4-thiadiazolidin-5-ylidene]benzamide

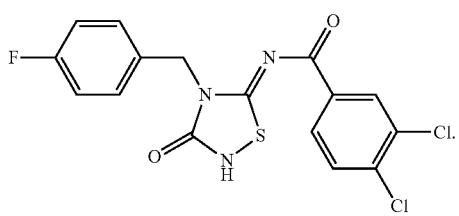 [SMILES: O=C(/N=c1\s[nH]c(=O)n1Cc1ccc(F)cc1)c1ccc(Cl)c(Cl)c1]

Example 8

The following compounds, were (a to d, f, k, l, o to r and w), or may be prepared using the procedures described in Example 1 with the exceptions that in step (i):

(i) no base is used in the first step to ensure coupling of the isothiocyanate derivative to the primary nitrogen of the urea derivative;

(ii) 20% DMF in acetonitrile is used as the solvent; and (iii) the reaction mixture was stirred for 48 h at 80° C.

a) 1,5-(3,4-Dichlorophenylamino)-2-(4-methoxybenzyl)-[1,2,4]thiadiazol-3-one

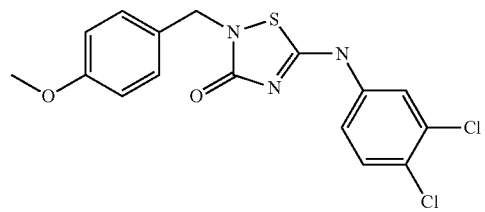 [SMILES: COc1ccc(Cn2sc(Nc3ccc(Cl)c(Cl)c3)nc2=O)cc1]

1H NMR (500 MHz, DMSO-$d_6$) δ ppm 3.74 (s, 3H) 4.72 (s, 2H) 6.92 (q, J=5.13 Hz, 2H) 7.24 (q, J=5.13 Hz, 2H) 7.45 (dd, J=8.79, 2.44 Hz, 1H) 7.62 (d, J=8.79 Hz, 1H) 8.04 (d, J=2.44 Hz, 1H), ESI MS m/z=382 [M+H]+., HPLC purity: 100%;

b) 1,5-(3,4-dichlorophenylamino)-2-(4-chlorobenzyl)-[1,2,4]thiadiazol-3-one

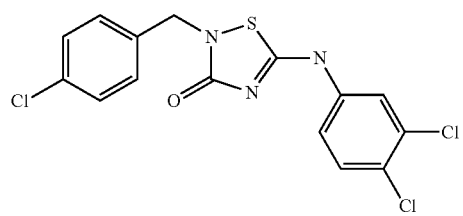 [SMILES: O=c1nc(Nc2ccc(Cl)c(Cl)c2)sn1Cc1ccc(Cl)cc1]

1H NMR (500 MHz, DMSO-$d_6$) δ ☐ppm 4.81 (s, 2H) 7.32 (d, J=8.55 Hz, 2H) 7.42-7.47 (m, 3H) 7.63 (d, J=8.79 Hz, 1H) 8.05 (d, J=2.44 Hz, 1H), MS: ESI MS m/z=386 [M+H]$^+$; HPLC purity: 95%;

c) 1,5-(3,4-dichlorophenylamino)-2-(3,4-difluorobenzyl)-[1,2,4]thiadiazol-3-one

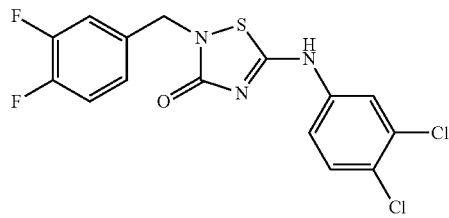 [SMILES: O=c1nc(Nc2ccc(Cl)c(Cl)c2)sn1Cc1ccc(F)c(F)c1]

1H NMR (500 MHz, DMSO-d$_6$) δ ppm 4.80 (s, 3H) 7.14-7.17 (m, 1H) 7.36-7.47 (m, 3H) 7.63 (d, J=8.79 Hz, 1H) 8.05 (d, J=2.44 Hz, 1H), ESI MS m/z=388 [M+H]$^+$; HPLC purity: 100%;

d) 1,5-(3,4-dichlorophenylamino)-2-(3-fluorobenzyl)-[1,2,4]thiadiazol-3-one

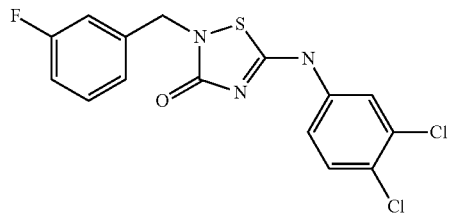 [SMILES: O=c1nc(Nc2ccc(Cl)c(Cl)c2)sn1Cc1cccc(F)c1]

1H NMR (500 MHz, DMSO-d$_6$) δ ppm 4.83 (s, 2H) 7.09-7.18 (m, 3H) 7.38-7.48 (m, 2H) 7.63 (d, J=8.79 Hz, 1H) 8.05 (d, J=1.22 Hz, 1H), MS: 371 [M+H]$^+$, HPLC purity: 97%;

e) 1,5-(3,4-dichlorophenylamino)-2-(benzyl)-[1,2,4]thiadiazol-3-one

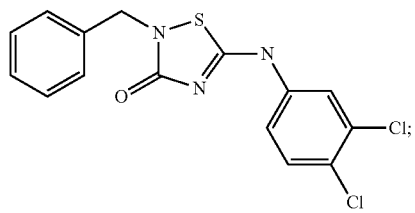 [SMILES: O=c1nc(Nc2ccc(Cl)c(Cl)c2)sn1Cc1ccccc1]

f) 5-(3,4-dichlorophenylamino)-2-phenethyl-[1,2,4]thiadiazol-3-one

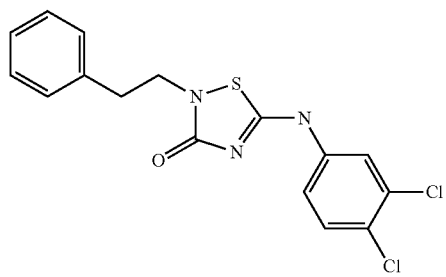 [SMILES: O=c1nc(Nc2ccc(Cl)c(Cl)c2)sn1CCc1ccccc1]

1H NMR (500 MHz, DMSO-d$_6$) δ ppm 2.89 (t, J=7.08 Hz, 2H) 3.87 (t, J=7.08 Hz, 2H) 7.19-7.34 (m, 5H) 7.42 (dd, J=8.79, 2.44 Hz, 1H) 7.62 (d, J=8.79 Hz, 1H) 8.02 (d, J=1.71 Hz, 1H), MS: 367 [M+H]$^+$, HPLC purity: 97%;

g) 2-[2-[(4-chlorophenyl)-methyl-amino]ethyl]-5-[(3,4-dichlorophenyl)amino]-1,2,4-thiadiazol-3-one

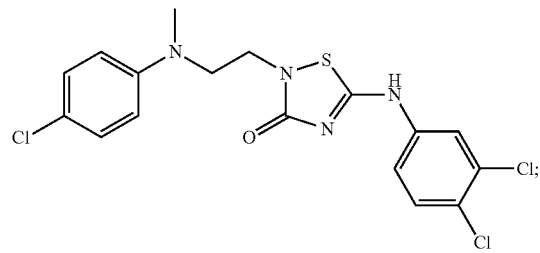 [SMILES: CN(CCn1sc(Nc2ccc(Cl)c(Cl)c2)nc1=O)c1ccc(Cl)cc1]

h) 2-[2-(4-chlorophenyl)sulfanylethyl]-5-[(3,4-dichlorophenyl)amino]-1,2,4-thiadiazol-3-one

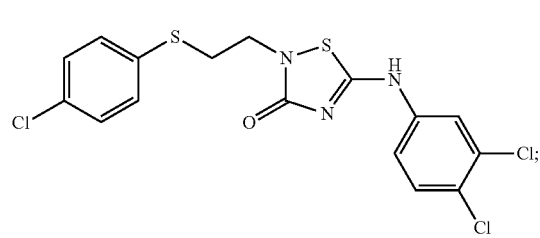 [SMILES: O=c1nc(Nc2ccc(Cl)c(Cl)c2)sn1CCSc1ccc(Cl)cc1]

i) 3-[[5-[(4-chlorophenyl)amino]-3-oxo-1,2,4-thiadiazol-2-yl]methyl]-N-methyl-benzamide

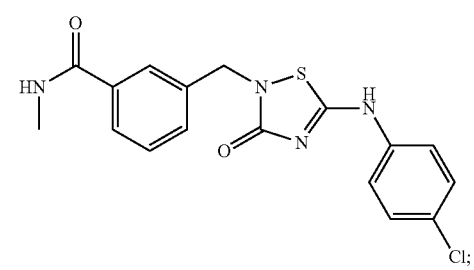 [SMILES: CNC(=O)c1cccc(Cn2sc(Nc3ccc(Cl)cc3)nc2=O)c1]

j) 5-[(6-chloro-3-pyridyl)amino]-2-[(3,4-difluorophenyl)methyl]-1,2,4-thiadiazol-3-one

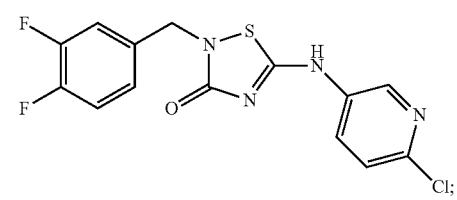 [SMILES: O=c1nc(Nc2ccc(Cl)nc2)sn1Cc1ccc(F)c(F)c1]

k) 2-[(3,4-difluorophenyl)methyl]-5-[[4-(trifluoromethyl)phenyl]amino]-1,2,4-thiadiazol-3-one

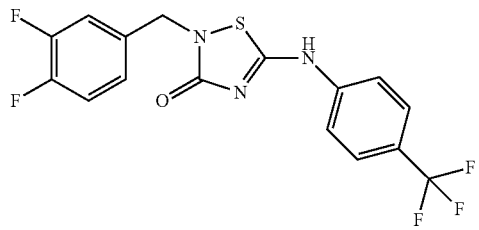 [SMILES: O=c1nc(Nc2ccc(C(F)(F)F)cc2)sn1Cc1ccc(F)c(F)c1]

1H NMR (500 MHz, DMSO-d$_6$) δ ppm 4.82 (s, 2H) 7.13-7.21 (m, 1H) 7.36-7.48 (m, 2H) 7.72-7.77 (m, 2H) 7.78-7.84 (m, 2H), MS: 388 [M+H], HPLC purity: 95%;

l) 2-[(3,4-difluorophenyl)methyl]-5-[[4-(trifluoromethoxy)phenyl]amino]-1,2,4-thiadiazol-3-one

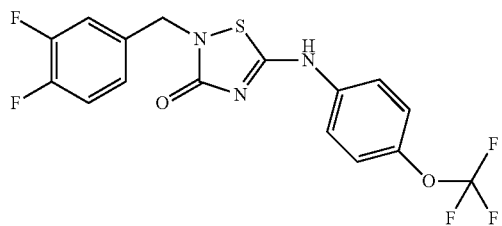 [SMILES: O=c1nc(Nc2ccc(OC(F)(F)F)cc2)sn1Cc1ccc(F)c(F)c1]

1H NMR (500 MHz, DMSO-d$_6$) δ ppm 4.79 (s, 2H) 7.12-7.20 (m, 1H) 7.33-7.49 (m, 4H) 7.70 (d, J=9.03 Hz, 2H), MS: 404 [M+H]$^+$, HPLC purity: 100%;

m) 5-[(4-chlorophenyl)amino]-2-[1-(4-chlorophenyl)cyclopropyl]-1,2,4-thiadiazol-3-one

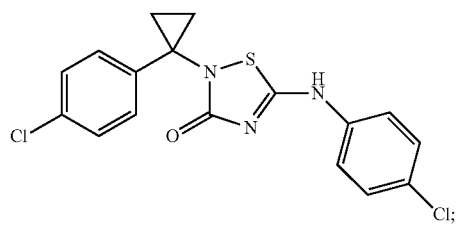 [SMILES: O=c1nc(Nc2ccc(Cl)cc2)sn1C1(c2ccc(Cl)cc2)CC1]

n) 5-[(3,4-dichlorophenyl)methylamino]-2-[(3,4-difluorophenyl)methyl]-1,2,4-thiadiazol-3-one

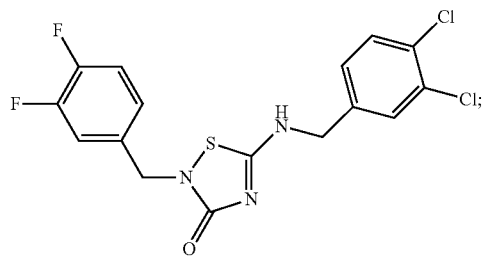 [SMILES: O=c1nc(NCc2ccc(Cl)c(Cl)c2)sn1Cc1ccc(F)c(F)c1]

o) 2-[(4-methoxyphenyl)methyl]-5-[[4-(trifluoromethyl)phenyl]amino]-1,2,4-thiadiazol-3-one

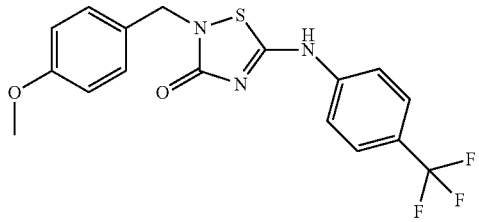 [SMILES: COc1ccc(Cn2sc(Nc3ccc(C(F)(F)F)cc3)nc2=O)cc1]

1H NMR (500 MHz, DMSO-d$_6$) δ ppm 3.74 (s, 3H) 4.74 (s, 2H) 6.89-6.97 (m, 2H) 7.22-7.29 (m, 2H) 7.71-7.76 (m, 2H) 7.76-7.82 (m, 2H), MS: 382 [M+H]$^+$, HPLC purity: 100%;

p) 2-[(4-chlorophenyl)methyl]-5-[[4-(trifluoromethyl)phenyl]amino]-1,2,4-thiadiazol-3-one

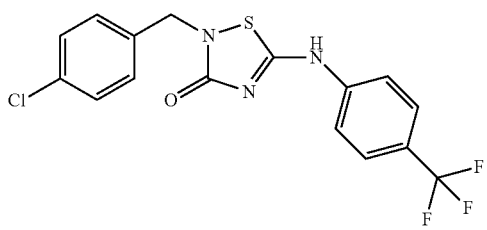 [SMILES: O=c1nc(Nc2ccc(C(F)(F)F)cc2)sn1Cc1ccc(Cl)cc1]

1H NMR (500 MHz, DMSO-d$_6$) δ ppm 4.82 (s, 2H) 7.29-7.36 (m, 2H) 7.41-7.47 (m, 2H) 7.73-7.77 (m, 2H) 7.77-7.83 (m, 2H), MS: 387 [M+H], HPLC purity: 100%;

q) 2-[(3-fluorophenyl)methyl]-5-[[4-(trifluoromethyl)phenyl]amino]-1,2,4-thiadiazol-3-one

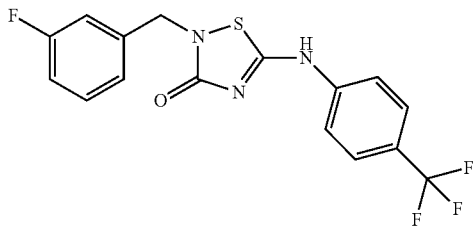 [SMILES: O=c1nc(Nc2ccc(C(F)(F)F)cc2)sn1Cc1cccc(F)c1]

1H NMR (500 MHz, DMSO-d$_6$) δ ppm 4.84 (s, 2H) 7.10-7.20 (m, 3H) 7.37-7.46 (m, 1H) 7.72-7.78 (m, 2H) 7.77-7.84 (m, 2H), MS: 370 [M+H], HPLC purity: 100%;

r) 2-[phenylethyl]-5-[[4-(trifluoromethyl)phenyl]amino]-1,2,4-thiadiazol-3-one

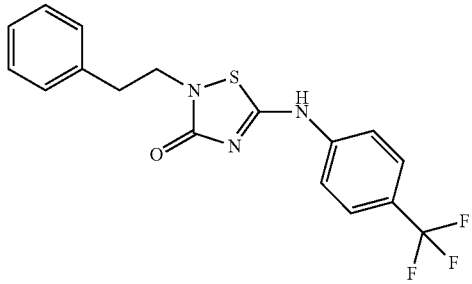 [SMILES: O=c1nc(Nc2ccc(C(F)(F)F)cc2)sn1CCc1ccccc1]

1H NMR (500 MHz, DMSO-$d_6$) δ ppm 2.90 (t, J=7.08 Hz, 2H) 3.88 (t, J=7.08 Hz, 2H) 7.19-7.34 (m, 5H) 7.71-7.76 (m, 2H) 7.76-7.82 (m, 2H), MS: 360 [M+H]+, HPLC purity: 95%;

s) 2-[(4-methoxyphenyl)methyl]-5-[[4-(trifluoromethoxy)phenyl]amino]-1,2,4-thiadiazol-3-one

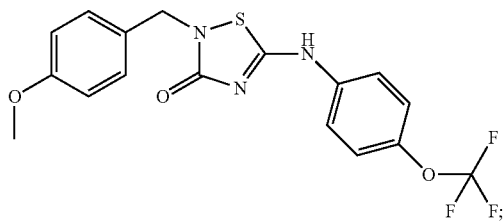 [SMILES: COc1ccc(Cn2sc(Nc3ccc(OC(F)(F)F)cc3)nc2=O)cc1]

t) 2-[(4-chlorophenyl)methyl]-5-[[4-(trifluoromethoxy)phenyl]amino]-1,2,4-thiadiazol-3-one

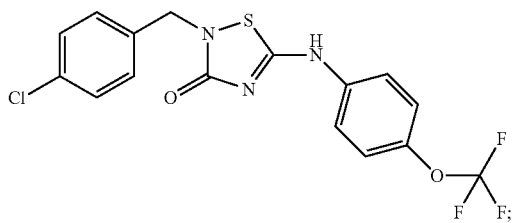 [SMILES: O=c1nc(Nc2ccc(OC(F)(F)F)cc2)sn1Cc1ccc(Cl)cc1]

u) 2-[(3-fluorophenyl)methyl]-5-[[4-(trifluoromethoxy)phenyl]amino]-1,2,4-thiadiazol-3-one

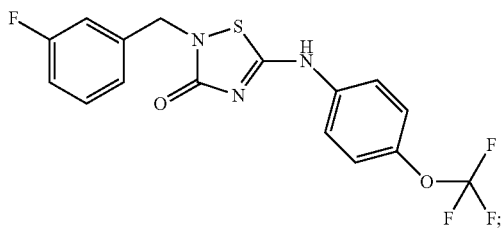 [SMILES: O=c1nc(Nc2ccc(OC(F)(F)F)cc2)sn1Cc1cccc(F)c1]

v) 2-[phenylethyl]-5-[[4-(trifluoromethoxy)phenyl]amino]-1,2,4-thiadiazol-3-one

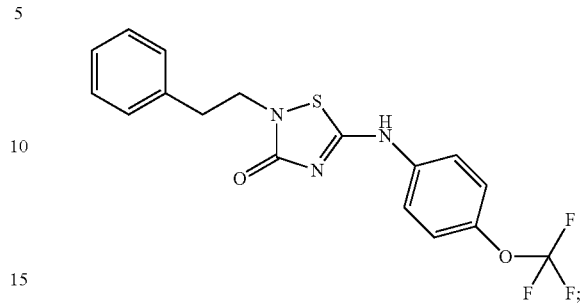

w) 4-[[2-[(3,4-difluorophenyl)methyl]-3-oxo-1,2,4-thiadiazol-5-yl]amino]benzonitrile

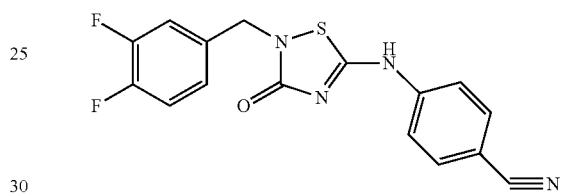

1H NMR (500 MHz, DMSO-$d_6$) δ ppm 4.82 (s, 2H) 7.13-7.20 (m, 1H) 7.36-7.48 (m, 2H) 7.75-7.82 (m, 2H) 7.82-7.88 (m, 2H), MS: 345 [M+H]$^+$, HPLC purity: 95%.

Biological Tests

Descriptions of the cancer cell lines including source, tumor type, and morphology may be obtained from the American Type Culture Collection (ATCC) or its website (wvww.atcc.org). The cell lines are both from primary tumors and metastatic sites (for example, MCF-7, MDA-MB231, HT-29, SKOV-3 and PC-3 among others tested).

Test A

Cell Proliferation Assay

Reagents

Dulbecco's modified Eagle's medium (D-MEM)+1000 mg/L Glucose+GlutaMAX™1+

Pyruvate (Gibco #21885-025)

V/V Foetal Bovine Serum (Gibco 10500-064)

5-bromo-2-deoxyuridine (BrdU)

30 Dimethyl sulfoxide (DMSO)

PC-3 cancer cell lines were propagated in D-MEM (Gibco 21885) supplemented with 10% Foetal calf serum. 15000 cells per well were seeded in 96 well plates and incubated overnight. The culture media was changed to serum-free D-MEM for 24 h. The culture media was then changed to serum free D-MEM containing either 0.2% DMSO as vehicle control or 0.3, 0.6, 1.2 or 2.5 μM (or 1.25, 2.5, 5, 10 μM (as indicated in Table 1 below)) of the selected compounds of Example 1 to Example 8 in 0.2% DMSO in quadruplicate. After 18 h incubation, BrdU was added according to manufacturer's recommendations. After 6 h incubation in the presence of BrdU, the culture media was removed and BrdU incorporation was measured using "Cell Proliferation ELISA, BrdU colorimetric" Roche (11647229001) according to manufacturer's recommendations.

Results

Proliferation rate of PC-3 cells are reduced by relevant concentrations of the test compounds as measured by BrdU incorporation. For example, in the above assay, the selected compounds of Example 1 to Example 8, relative to the vehicle control (which display a BrdU incorporation of 1 unit) displayed the following (approximate) units of BrdU incorporations at the indicated concentrations in Table 1 below.

TABLE 1

| Examples (No) | Units of BrdU incorporation | Conc (µM) |
|---|---|---|
| 1 | 0.39 | 0.6 |
| 2c | 0.34 | 0.6 |
| 2e | 0.17 | 5 |
| 2g | 0.14 | 10 |
| 3 | 0.70 | 10 |
| 4a | 0.309 | 10 |
| 4b | 0.72 | 10 |
| 4c | 0.393 | 10 |
| 4d | 0.612 | 10 |
| 4e | 0.355 | 10 |
| 4i | 0.10 | 5 |
| 4l | 0.20 | 10 |
| 4m | 0.23 | 10 |
| 4n | 0.17 | 2.5 |
| 4o | 0.28 | 10 |
| 4p | 0.26 | 10 |
| 5a | 0.37 | 10 |
| 5b | 0.14 | 10 |
| 6 | 0.42 | 1.25 |
| 8a | 0.04 | 2.5 |
| 8b | 0.18 | 2.5 |
| 8c | 0.07 | 1.25 |
| 8f | 0.08 | 5 |
| 8k | 0.04 | 5 |
| 8l | 0.10 | 5 |
| 8p | 0.07 | 5 |
| 8q | 0.15 | 5 |
| 8r | 0.58 | 5 |
| 8w | 0.28 | 5 |

Test B

In Vivo Mouse Model—Test 1

5 week old Athymic BALB/cA nude mice are delivered from Taconic (Denmark) and kept under barrier conditions for 1 week acclimatisation. At 6 weeks, 17 mice are injected subcutaneously on the flank with $1.8 \times 10^6$ MDA-MB-231 human breast cancer cells (LGC Promochem-ATCC) in a 50/50 v/v solution of phosphate buffered saline (PBS) (Gibco 10010-015, Invitrogen) Matrigel HC (BD Biosciences).

After 11 days, palpable tumors are observed in 16 mice. 2 mice are sacrificed and the tumors dissected and examined. 2 groups of 7 mice each are treated once daily by intraperitoneal injections of 1-10 mg/kg bodyweight of test compound in 79% PBS/20% Solutol HS 15(BASF)/1% DMSO or vehicle control respectively for 5-30 days. The mice are sacrificed by cervical dislocation and tumors are dissected.

Histology

The tumor tissue is fixated overnight in PBS (containing 4% w/v paraformaldehyde (Scharlau PA0095, Sharlau Chemie SA, Spain) at +4° C. The tumor tissue is cryopreserved by 24 hour incubation in PBS containing 30% w/v sucrose (BDH #102745C (www.vwr.com) at +4° C. and is embedded in Tissue-Tek embedding media (Sakura Finetek Europa BV, Netherlands). 10 µm cryosections are generated and stained with Mayers Hematoxylin (Dako) for 5 minutes and destained for 3×10 minutes in tap water. Slides are mounted using Dako faramount aqueous mounting medium and are examined using a Nikon Eclipse TS 100 microscope documented using a Nikon coolpix 4500.

The tumors from mice treated with test compound and vehicle are analyzed for morphology by microscopic examination of hematoxylin stained cryosections.

In Vivo Mouse Model—Test 2

The above test procedure is followed, but 16 (rather than 17) mice are injected subcutaneously.

After 6 days, palpable tumors my be observed in the 16 mice. 2 groups of 8 mice each are treated once daily by intraperitoneal injections of 7.5 mg/kg bodyweight of test compound in 79% PBS/20% Solutol HS 15(BASF)/1% DMSO or vehicle control respectively for 27 days. Tumor size is measured by calliper every third day.

The results of the tumor area in the first group of mice (treated with test compound) are compared against the second ('untreated') group of mice after a certain number of days.

As will be appreciated, Test B as described above provides one of many potential in vivo xenograft models. Modifications to Test B above may be made (e.g. by changing some or all of: the formulation of the test compounds; the cell line; and the type of mice used).

Test C

Activation of AMPK and S-79 ACC

Test Compound

Selected compounds of Examples 1, 4 to 6 and 8 were prepared. A stock solution of 10 µM was prepared by dissolving the compound in 100% DMSO.

Cell Line and Cell Culture

Human PC3 cells were purchased from LGC Promochem-ATCC (ATCC catalog no CRL-1435). PC3 cells were maintained in Dulbecco's modified Eagle's medium (Gibco 21885) containing 5% fetal bovine serum (Gibco 10500-064), 25 µg/ml Gentamicin (Gibco 20 15750) and 1× non essential amino acids (Gibco 11140). The cells were incubated in a humidified atmosphere of 5% CO2 at 37° C. and passaged every 3 days by trypsinization. For experiments, PC3 cells were cultured in complete medium with 10% fetal bovine serum in 60-mm-diameter dishes, grown to 70-80% confluence and cultured in serumfree Dulbecco's modified Eagle's medium for 5 h. Cells were then treated with 10 µM of the compound of Example 1 for 24 h. The final concentration of DMSO did not exceed 0.1%, which did not affect AMPK or eEF2 phosphorylation (0.1% DMSO was used as control).

Western Blot Analysis

PC3 cells were lysed in buffer (100 mM TRIS pH 6.8, 2% w/v Sodium dodecylsulfate (SDS), 10 mM NaF, 10 mM 3-glycerophosphate, 1 mM Na Vanadate). Cell debris is removed by centrifugation at 14,000×g for 15 min at 4° C. and the resulting supernatant is used for Western blotting. Protein concentrations of the lysates were measured using a BCA protein assay kit (Pierce #23225). For Western blotting, 15 µg protein was loaded in each well of a 4-12% bis/tris gel for AMPK or S-79 ACC detection (Criterion precast gel Bio-Rad #345-0117) and run according to manufacturers recommendation. Gels were blotted onto a nitrocellulose filters (Hybond-C extra Amersham #RPN203E). Filters were blocked in 20 mM TRIS pH 7.5, 137 mM NaCl, 25% v/v Tween20 and 5% w/v fat free powdered milk for 30 min. Filters were incubated overnight in blocking solution with phospho-AMPK (Thr172) or phospho-acetyl CoA carboxylase (Cell signalling #2531 and #3661) or with a pan-AMPK antibody (Cell signalling #2532).

Filters were washed in 20 mM TRIS pH 7.5, 137 mM NaCl, 25% v/v Tween20 for 3×5 min.

Filters were incubated in blocking solution with secondary antibody, peroxidase conjugated Goat anti-rabbit IgG (Jackson immunoResearch #111-035-003) at room temperature for 1 h. Filters were washed as above for 3×10 min. Signal was developed with SuperSignal West Dura ECL kit (Pierce #1859024) and exposed to Hyperfilm ECL Amersham #28906837).

Results

The Western blot result showed that the compounds of selected compounds from Examples 1, 4 to 6 and 8 stimulated the phosphorylation of Thr-172 of the AMPK ϵ-subunit (in comparison to control) and increased production of phosphorylated acetyl co-enzyme A (a substrate of AMPK), as depicted by FIGS. 1 and 2.

Test D

In vitro cytotoxicity data with several cell lines in a 96 well plate

SRB Cytotoxicity Study

Cells are seeded and grown in the presence of varying concentrations of test compound(s) for a period of 3 days (72 hours). The cells are then fixed to the plate and exposed to the dye sulphorhodamine B (SRB). The varying amounts of inhibition of proliferation produces a standard curve from which the $IC_{50}$ value is determined.

Section A: Seeding the Cells into the Plate 96 well plates in this assay are seeded at seeding density determined for each cell line accordingly.

Adherent Cells:

1. Harvest cells and count. All procedures associated with harvesting and preparing cell suspensions will be carried out in a Class II hood.
2. Assay uses a sterile 96 well plate cell culture plate (Microtest flat bottom tissue culture plate, Falcon 3072).
3. Dilute cells to appropriate seeding density.
4. Add 100 μL of the cell suspension to wells B1 to G12.
5. Add 100 μL of media to all Blank wells (A1 to A12, H1 to H12).
6. Incubate plate(s) overnight at 37° C. in a 5% $CO_2$ incubator.

Suspension Cells:

1. Harvest cells and count. All procedures associated with harvesting and preparing cell suspensions will be carried out in a Class II hood.
2. Assay uses a sterile 96 well plate cell culture plate (Microtest flat bottom tissue culture plate, Falcon 3072).
3. Dilute cells to appropriate seeding density.
4. Add 100 μL of the cell suspension to wells B1 to G12.
5. Add 100 μL of media to all Blank wells (A1 to A12, H1-H12).
6. Add drugs to cells immediately after plating.

Section B: Adding Test Compound(s) to Cells

7. Prepare compound plate for test compound(s) and transfer diluted compound to prepared assay plate in section A.
8. On compound plate add 100 μL of cell culture medium to well B3-G3 to B10-G10.
9. Dilute the test articles to 250 μM in the cell culture medium in a separate tube, which will make start concentration of 50 μM. Stock concentration of test compound(s) is 10 mM, therefore dilute 1:40 to obtain 250 μM concentration.
10. Add 200 μL of the diluted batch of drug to empty wells B2 to G2 and mix by pipetting up and down 3 times.
11. Transfer 100 μL from each of these wells (using a multichannel pipette) to wells B2-G2 etc and continue to dilute 1:2 across the plate to column 10. Discard the excess 100 μL from each row in column 10. Column 11 contains DMSO control. Row 12 contains 100 μL blank medium.
12. DMSO control same as drug: dilute 100% DMSO 1:40 in medium. Pipette 100 μL to empty row 11 on compound plate. From this 25 μL will be added to assay plate containing cells, which will give end concentration of 0.5%.

Blank control: Pipette 100 μL blank medium to row 1 and 12, 25 μL form this will be added to assay plate containing cells.

13. Using a new set of tips, transfer the drug dilutions from the compound plate onto the assay plate containing the cells (25 μL of diluted drug transferred to the 100 μL of cells in the assay plate. The end volume will be 125 μL). Start with lowest drug concentrations.
14. Incubate the assay plate at 37° C. in a 5% $CO_2$ incubator for 3 days.

Section C: Fixing and Staining the Cells

At the end of the incubation period the cells will need to be fixed and the SRB assay performed as described below:

1. Transfer the plate from the incubator in the cell culture suite to 4° C., leave cells for an hour.
2. Adherent cell lines: Fix cells to the plate by carefully adding 30 μL of cold 50% v/v Trichloroacetic acid (TCA BDH 102863H) to the cell culture medium already in the wells so the final concentration of TCA is 10% v/v.

Suspension cell lines: Fix cells to the plate by carefully adding 30 μL of cold 80% v/v Trichloroacetic acid (TCA BDH 102863H) to the cell culture medium already in the wells so the final concentration of TCA is 16% v/v.

1. Incubate at 4° C. for 1 hour.
2. Submerge plate in a plastic container containing distilled water such that each well fills with water. Leave to soak for 1 minute. Flick off wash solution into the sink and repeat this washing step a further four times. Finally, flick off wash solution and leave to air dry.
3. When wells are completely dry add 100 μl of 0.4% w/v Sulforhodamine B (SRB Sigma S1402) in 1% v/v acetic acid to each well and incubate at room temperature for 30 minutes.
4. Flick off SRB and wash four times by submerging the plates for 1 minute in 1% v/v acetic acid. Flick off wash solution and leave to air dry.
5. When wells are completely dry add 100 μl of 10 mM Tris base pH 10.5 (pH adjusted to 10.5 using sodium hydroxide solution). Place on a plate shaker and mix for 5 min. Read the plate at 564 nm using the SPECTRAmax microplate spectrophotometer acquiring data.

Test E

Clonogenic Assay Results

Section A: Seeding the Assay Plates 24 well plates (Falcon Cat no: 353047) in this assay are seeded at seeding density determined for each cell line accordingly.

Base Agar:

1. Melt 1.6% Agar (invitrogen Select Agar) in microwave, and cool to 40-42° C. in a waterbath.
2. Warm cell culture Media+20% FBS+2× of any other cell culture supplements required to 40-42° C. in waterbath. Allow at least 30 minutes for temperature to equilibrate.
3. Mix equal volumes of the two solutions to give 0.8% Agar+Media+10% FBS+1× cell culture supplements.
4. Add 0.2 ml/well, allow setting. The plates can be stored at 4° C. for up to 1 week.

Top Agar:

1. Melt 0.8% Agar (invitrogen Select Agar) in microwave, and cool to 40° C. in a waterbath.
2. Warm Media+20% FBS+2× of any other cell culture supplements required to the same temperature.

3. Harvest cells and count. All procedures associated with harvesting and preparing cell suspensions will be carried out in a Class II hood.
4. Dilute cells in Media to appropriate seeding density.
5. Label the 24 well plates with base agar appropriately (if the plate is stored in the refrigerator, remove the plate from 4° C. about 30 minutes prior to plating to allow them to warm up to room temperature).
6. For plating mix equal volumes of Media+20% FBS+2× cell culture supplements+cells and soft Agar 0.8% solution to a 15 ml capped centrifuge tube, mix gently and add 0.2 ml to each replicate well (usually plate out in quadruplicate).
7. Incubate plate(s) overnight at 37° C. in a 5% $CO_2$ incubator Section B: Adding Test Compound to Cells
1. Prepare compound plate for test compound(s) and then transfer diluted compound to prepared assay plate in section A.
2. Dilute the test compound(s) to 120 µM in the cell culture medium in a separate tube, which will make start concentration of 40 µM.
Stock concentration of test compound(s) is 10 mM, therefore dilute 1:83.3 to obtain 120 µM concentration.
3. Make dilutions of the drug test solution by 1:2, 3 times from the start concentration of 120 µM to prepare the test drug concentrations at 20, 10 and 5 µM.
4. Transfer 200 µL from each test concentration to each well by quadruplicate. Column 6 contains 40 µM test compound(s). Column 5 contains 20 µM test compound(s), Column 4 contains 10 µM test compound(s), and Column 3 contains 5 µM test compound(s).
5. DMSO controls same as drug: dilute 100% DMSO 1:83.3 in medium. Pipette 200 µL to Column 2 on compound plate by quadruplicate, which will give end concentration of 0.4%.
6. Blank control: Pipette 200 µL blank medium per well to Column 1 by quadruplicate.
7. Incubate the assay plate at 37° C. in a 5% $CO_2$ incubator for 2-3 weeks.

Section C: Staining and Counting the Cell Colonies
At the end of the incubation period the cell colonies will need to be stained and count as described below:
1. Mark the bottom of each well dividing each well at least in four sections.
2. Stain plates with 0.2 ml of 0.005% Crystal Violet for 1 hour at 37° C. 5% $CO_2$ in a humidified incubator.
3. Count the colonies per well for each test group using a dissecting microscope.
4. To consider a group of cells as a colony at least each colony must have 50 cells.
5. Calculate the average of number of colonies of each well per group and calculate the % of inhibition of cell colonies formation produced by test compound using the formula % T/C, in which T is the test group and C is the controls.

Test F
Dephosphorylation of PP2C Assay
Hyperphosporylated AMPK trimer 10 (ng) (α1/β1/γ1) from Invitrogen (PV4672) was incubated in a buffer containing: 40 mM Hepes pH 7.45, 2 mM $MnCl_2$, 0.5 mM DTT and 0.125 ng recombinant PP2C-α1 (Abcam Ab51205) in the presence or absence of potential inhibitors of the interaction/enzymatic reaction in at total volume of 10 µL for 20 minutes in 30° C. The reaction was terminated by addition of 40 µL stop solution containing 1% Bovine Serum Albumin (BSA), 10 mM EDTA and anti Phospho-AMPKα (Thr172) Antibody (cell signaling #2531) at a dilution of 1/1000. The samples were transferred to glutathione coated 96 well plated (Pierce #15140) and incubated O/N at +4° C. The plate was washed 3×200 µL in PBS/0.05% Triton X-100. The plate was incubated with PBS/1% BSA and horse radish peroxidase conjugated goat-anti rabbit antibody (Jackson immunoresearch Laboratories Inc. #111-035-003) at a dilution of 1/10 000 for 2 h in room temperature. The plate was washed 3×200 µL in PBS/0.05% Triton X-100. The assay was developed by addition of 100 µL Liquid Substrate System for ELISA (Sigma, T0440) for 5-30 min. The developing reaction was terminated by addition of 25 µL 1M in each well. Absorbance was measured at 450 nm, where absorbance correlates to amount p-T172 AMPK.

Results
As illustrated in FIG. 3, the compounds of Example 1 and Example 2c have the ability to reduce PP2C-α1 mediated dephosphorylation of AMPK.

The invention claimed is:
1. A method of treating diabetes in a patient, comprising administering an effective amount of a compound to the patient, wherein the compound is represented by formula I,

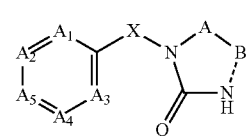

I

A represents S;
B represents C(—NH—W-D);
the bond between B and the NH group is a double bond;
X represents -Q-[$CR^xR^y$]$_n$—;
W represents —[$CR^xR^y$]$_m$— or —C(O)—[$CR^xR^y$]$_p$—;
Q represents a bond, —N($R^a$)—, —S—, or —O—;
$A_1$ to $A_5$ respectively represent C($R^1$), C($R^2$), C($R^3$), C($R^4$) and C($R^5$), or, alternatively, up to two of $A_1$ to $A_5$ may independently represent N;
D represents phenyl, pyridyl or pyrimidinyl each of which is substituted by one or more $R^6$ groups;
$R^x$ and $R^y$, on each occasion when used herein, are independently selected from H, halo, $C_{1-6}$ alkyl (optionally substituted by one or more halo atoms), aryl (optionally substituted by one or more halo atoms) or $R^x$ and $R^y$ are linked to form, along with the carbon atom to which they are attached, a non-aromatic 3- to 8-membered ring, optionally containing 1 to 3 heteroatoms selected from O, S and N, which ring is itself optionally substituted by one or more substituents selected from halo or $C_{1-6}$ alkyl (optionally substituted by one or more halo atoms);
$R^1$ to $R^5$ independently represent H, halo, —$R^7$, —$CF_3$, —CN, —$NO_2$, —C(O)$R^7$, —C(O)O$R^7$, —C(O)—N($R^{7a}$)$R^{7b}$, —N($R^{7a}$)$R^{7b}$, —N($R^7$)$_3{}^+$, —S$R^7$, —O$R^7$, —NH(O)$R^7$, —SO$_3R^7$, aryl or heteroaryl (which aryl and heteroaryl groups are themselves optionally and independently substituted by one or more groups selected from halo and $R^{16}$), or any two of $R^1$ to $R^5$ which are adjacent to each other are optionally linked to form, along with two atoms of the essential benzene ring in the compound of formula I, an aromatic or non-aromatic 3- to 8-membered ring, optionally containing 1 to 3 heteroatoms selected from O, S and N, which ring is itself optionally substituted by one or more substituents selected from halo, —R⁷, —OR⁷ and ═O;

R⁶ independently represents, on each occasion when used herein, cyano, halo, $C_{1-6}$ alkyl (which alkyl group is substituted by one or more halo atoms), —OR⁸, —N(R⁸)C(O)R⁸, —NR⁹R¹⁰, —SR¹¹, —Si(R¹²)₃, —OC(O)R¹³, —C(O)OR¹³, —C(O)R¹⁴, —C(O) NR¹⁵ᵃR¹⁵ᵇ, —S(O)₂NR¹⁵ᶜR¹⁵ᵈ, aryl or heteroaryl (which aryl and heteroaryl groups are themselves optionally and independently substituted by one or more groups selected from halo and R¹⁶), or any two R⁶ groups which are adjacent to each other are optionally linked to form, along with two atoms of the essential benzene ring in the compound of formula I, an aromatic or non-aromatic 3- to 8-membered ring, optionally containing 1 to 3 heteroatoms selected from O, S and N, which ring is itself optionally substituted by one or more substituents selected from halo, —R⁷, —OR⁷ and ═O;

R⁷, on each occasion when used herein, is selected from H or $C_1$-$C_6$ alkyl, $C_1$-$C_6$ cycloalkyl, aryl and heteroaryl (wherein the latter four groups are optionally substituted by one or more halo atoms);

R⁷ᵃ and R⁷ᵇ are independently selected from H, or $C_1$-$C_6$ alkyl, $C_1$-$C_6$ cycloalkyl, aryl and heteroaryl, or R⁷ᵃ and R⁷ᵇ are optionally linked to form, along with the nitrogen atom to which they are attached, an aromatic or non-aromatic 3- to 8-membered ring, optionally containing 1 to 3 heteroatoms selected from O, S and N, which ring is itself optionally substituted by one or more substituents selected from halo, —R⁷, —OR⁷ and ═O;

Rᵃ, R⁸, R⁹, R¹⁰, R¹¹, R¹², R¹³, R¹⁴, R¹⁵ᵃ, R¹⁵ᵇ, R¹⁵ᶜ and R¹⁵ᵈ, on each occasion where used herein, independently represent H or R¹⁶;

R¹⁶ represents, on each occasion when used herein, $C_{1-6}$ alkyl optionally substituted by one or more halo atoms;

n represents 0 or, more preferably, 1 or 2;

m represents 2 or, more preferably, 1 or 0;

p represents 2 or, more preferably, 1 or 0;

or a pharmaceutically acceptable salt or solvate, or a pharmaceutically functional derivative thereof.

2. The method of claim 1, wherein each R⁶ independently represents —CN, —CF₃, —OCF₃, –F or –Cl.

3. The method of claim 1, wherein at least one of $A_1$ to $A_5$ is not (C—H).

4. The method of in claim 1, wherein Rˣ and Rʸ are independently selected from H, $C_{1-6}$ alkyl (optionally substituted by one or more fluoro atoms), and aryl (optionally substituted by one or more halo atoms) or Rˣ and Rʸ are linked to form, along with the carbon atom to which they are attached, a non-aromatic 3- to 6-membered unsubstituted ring.

5. The method of claim 1, wherein X represents —CH₂—, —CH₂CH₂—, —O—CH₂CH₂—, —N(CH₃)—CH₂CH₂—, —S—CH₂CH₂—, 1,1-cyclopropyl or —C(H)(4)-chlorophenyl)-.

6. The method of claim 1, wherein at least one of R¹ to R⁵, when present, represents halo, —R⁷, —CF₃, —CN, —C(O)R⁷, —C(O)OR⁷, —C(O)—N(R⁷ᵃ)R⁷ᵇ, —N(R⁷)₃⁺, —SR⁷, —OR⁷ or —NH(O)R⁷, or any two of R¹ to R⁵ which are adjacent to each other are optionally linked to form, along with two atoms of the essential benzene ring in the compound of formula I, and aromatic or non-aromatic 3- to 8-membered ring, optionally containing 1 to 3 heteroatoms selected from O, S and N, which ring is itself optionally substituted by one or more substituents selected from halo, —R⁷, —OR⁷ and ═O.

7. The method of claim 6, wherein at least one of R¹ to R⁵, when present, represents 4H-[1,2,4]-triazolyl, —OR⁷, —Cl, —F, —CF₃, —CN or —C(O)—N(R⁷ᵃ)R⁷ᵇ.

8. The method of claim 1, wherein R⁶ independently represents —C(O)NR¹⁵ᵃR¹⁵ᵇ, cyano, —NO₂, —Br, —Cl, —F, $C_{1-6}$ alkyl (which alkyl group is substituted by one or more halo atoms), —OR⁸, —NR⁹R¹⁰, —SR¹¹, —C(O) OR¹³, —C(O)R¹⁴, —S(O)₂NR¹⁵ᶜR¹⁵ᵈ, aryl or heteroaryl (which aryl and heteroaryl groups are themselves optionally and independently substituted by one or more groups selected from halo and R¹⁶), or any two R⁶ groups which are adjacent to each other are optionally linked to form, along with two atoms of the essential benzene ring in the compound of formula I, quinoline, tetrahydroquinoline, isoquinoline or tetrahydroisoquinoline, wherein the additional ring system of quinoline, tetrahydroquinoline, isoquinoline or tetrahydroisoquinoline moiety is itself optionally substituted by one or more substituents selected from halo, —R⁷, —OR⁷ and ═O.

9. The method of claim 8, wherein R⁶ independently represents $C_{1-6}$ alkyl (which alkyl group is substituted by one or more halo atoms), —CN, —OCF₃, —NO₂, —Br, —Cl, —F, —OR⁸, —NR⁹R¹⁰ or —SR¹¹.

10. The method of claim 1, wherein n represents 1 or 2; m represents 0 or 1; and/or p represents 0 or 1.

11. The method of claim 1, wherein W represents a direct bond, —CH₂—, —C(O)— or —C(O)CH₂—.

12. The method of claim 11, wherein W represents —C(O)— or —C(O)CH₂—.

13. The method of claim 1, which is selected from the group:

xix) 4-fluoro-N-[3-oxo-2-[[3-(trifluoromethyl)phenyl]methyl]-1,2,4-thiadiazol-5-yl]benzamide;

xx) 2-(4-fluorophenyl)-N-[3-oxo-2-[[3-(trifluoromethyl)phenyl]methyl]-1,2,4-thiadiazol-5-yl]acetamide;

xxi) 4-chloro-N-[2-[(3,4-difluorophenyl)methyl]-3-oxo-1,2,4-thiadiazol-5-yl]benzamide;

xxii) 4-chloro-N-[2-[(4-fluorophenyl)methyl]-3-oxo-1,2,4-thiadiazol-5-yl]benzamide;

xxiii) 4-chloro-N-[2-[(4-chlorophenyl)methyl]-3-oxo-1,2,4-thiadiazol-5-yl]benzamide;

xxiv) 4-chloro-N-[2-[2-(phenoxy)ethyl]-3-oxo-1,2,4-thiadiazol-5-yl]benzamide;

xxv) 4-chloro-N-[2-[2-[(4-chlorophenyl)-methyl-amino]ethyl]-3-oxo-1,2,4-thiadiazol-5-yl]benzamide;

xxvi) 4-chloro-N-[2-[2-(4-chlorophenyl)sulfanylethyl]-3-oxo-1,2,4-thiadiazol-5-yl]benzamide;

xxvii) 3,4-dichloro-N-[2-[1-(4-fluorophenyl)cyclopropyl]-3-oxo-1,2,4-thiadiazol-5-yl]benzamide;

xxviii) 3,4-dichloro-N-[2-[(4-fluorophenyl)methyl]-3-oxo-1,2,4-thiadiazol-5-yl]benzamide;

xxix) N-[2-[(4-fluorophenyl)methyl]-3-oxo-1,2,4-thiadiazol-5-yl]-4-methoxy-benzamide;

xxx) 2,6-dichloro-N-[2-[(4-fluorophenyl)methyl]-3-oxo-1,2,4-thiadiazol-5-yl]benzamide;

xxxi) 2,4-dichloro-N-[2-[(4-fluorophenyl)methyl]-3-oxo-1,2,4-thiadiazol-5-yl]benzamide;

xxxii) N-[2-[(4-fluorophenyl)methyl]-3-oxo-1,2,4-thiadiazol-5-yl]-4-(trifluoromethoxy)-benzamide;

xxxiii) N-[2-[(4-fluorophenyl)methyl]-3-oxo-1,2,4-thiadiazol-5-yl]-3,5-bis(trifluoromethyl)-benzamide;

xxxiv) 3,4-difluoro-N-[2-[(4-fluorophenyl)methyl]-3-oxo-1,2,4-thiadiazol-5-yl]benzamide;

xxxv) 2-chloro-6-fluoro-N-[2-[(4-fluorophenyl)methyl]-3-oxo-1,2,4-thiadiazol-5-yl]benzamide;
xxxvi) 3,5-difluoro-N-[2-[(4-fluorophenyl)methyl]-3-oxo-1,2,4-thiadiazol-5-yl]benzamide;
xxxviii) 5-(3,4-dichlorophenylamino)-2-(2-phenoxyethyl)-[1,2,4]thiadiazol-3-one;
xlvi) 1,5-(3,4-dichlorophenylamino)-2-(4-methoxybenzyl)-[1,2,4]thiadiazol-3-one;
xlvii) 1,5-(3,4-dichlorophenylamino)-2-(4-chlorobenzyl)-[1,2,4]thiadiazol-3-one;
xlviii) 1,5-(3,4-dichlorophenylamino)-2-(3,4-difluorobenzyl)-[1,2,4]thiadiazol-3-one;
xlix) 1,5-(3,4-dichlorophenylamino)-2-(3-fluorobenzyl)-[1,2,4]thiadiazol-3-one;
l) 1,5-(3,4-dichlorophenylamino)-2-(benzyl)-[1,2,4]thiadiazol-3-one;
li) 5-(3,4-dichlorophenylamino)-2-phenethyl-[1,2,4]thiadiazol-3-one;
lii) 2-[2-[(4-chlorophenyl)-methyl-amino]ethyl]-5-[(3,4-dichlorophenyl)amino]-1,2,4-thiadiazol-3-one;
liii) 2-[2-(4-chlorophenyl)sulfanylethyl]-5-[(3,4-dichlorophenyl)amino]-1,2,4-thiadiazol-3-one;
liv) 3-[[5-[(4-chlorophenyl)amino]-3-oxo-1,2,4-thiadiazol-2-yl]methyl]-N-methylbenzamide;
lv) 5-[(6-chloro-3-pyridyl)amino]-2-[(3,4-difluorophenyl)methyl]-1,2,4-thiadiazol-3-one;
lvi) 2-[(3,4-difluorophenyl)methyl]-5-[[4-(trifluoromethyl)phenyl]amino]-1,2,4-thiadiazol-3-one;
lvii) 2-[(3,4-difluorophenyl)methyl]-5-[[4-(trifluoromethoxy)phenyl]amino]-1,2,4-thiadiazol-3-one;
lviii) 5-[(4-chlorophenyl)amino]-2-[1-(4-chlorophenyl)cyclopropyl]-1,2,4-thiadiazol-3-one;
lix) 5-[(3,4-dichlorophenyl)methylamino]-2-[(3,4-difluorophenyl)methyl]-1,2,4-thiadiazol-3-one;
lxi) 2-[(4-methoxyphenyl)methyl]-5-[[4-(trifluoromethyl)phenyl]amino]-1,2,4-thiadiazol-3-one;
lxii) 2-[(4-chlorophenyl)methyl]-5-[[4-(trifluoromethyl)phenyl]amino]-1,2,4-thiadiazol-3-one;
lxiii) 2-[(3-fluorophenyl)methyl]-5-[[4-(trifluoromethyl)phenyl]amino]-1,2,4-thiadiazol-3-one;
lxiv) 2-[phenylethyl]-5-[[4-(trifluoromethyl)phenyl]amino]-1,2,4-thiadiazol-3-one;
lxv) 2-[(4-methoxyphenyl)methyl]-5-[[4-(trifluoromethoxy)phenyl]amino]-1,2,4-thiadiazol-3-one;
lxvi) 2-[(4-chlorophenyl)methyl]-5-[[4-(trifluoromethoxy)phenyl]amino]-1,2,4-thiadiazol-3-one;
lxvii) 2-[(3-fluorophenyl)methyl]-5-[[4-(trifluoromethoxy)phenyl]amino]-1,2,4-thiadiazol-3-one;
lxviii) 2-[phenylethyl]-5-[[4-(trifluoromethoxy)phenyl]amino]-1,2,4-thiadiazol-3-one; and
lxix) 4-[[2-[(3,4-difluorophenyl)methyl]-3-oxo-1,2,4-thiadiazol-5-yl]amino]benzonitrile.

14. The method of claim 1, wherein the diabetes is type 2 diabetes.

* * * * *

UNITED STATES PATENT AND TRADEMARK OFFICE
CERTIFICATE OF CORRECTION

PATENT NO. : 9,675,596 B2
APPLICATION NO. : 14/883190
DATED : June 13, 2017
INVENTOR(S) : Jacob Westman et al.

It is certified that error appears in the above-identified patent and that said Letters Patent is hereby corrected as shown below:

In the Claims

At Column 59, Claim number 6, Line number 66, delete "and" and replace with --an--.

At Column 60, Claim number 8, Line number 8, delete "–$NO_2$,".

At Column 60, Claim number 9, Line number 26, delete "–$NO_2$,".

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*